(12) United States Patent
Bracci et al.

(10) Patent No.: US 8,268,961 B2
(45) Date of Patent: Sep. 18, 2012

(54) ANTIBACTERIAL PEPTIDES AND ANALOGUES THEREOF

(75) Inventors: Luisa Bracci, Siena (IT); Andrea Giuliani, Siena (IT); Alessandro Pini, Siena (IT); Paolo Neri, Siena (IT)

(73) Assignee: Universita Degli Studi di Siena, Siena (IT)

( * ) Notice: Subject to any disclaimer, the term of this patent is extended or adjusted under 35 U.S.C. 154(b) by 748 days.

(21) Appl. No.: 11/632,449

(22) PCT Filed: Jul. 13, 2005

(86) PCT No.: PCT/IT2005/000397
§ 371 (c)(1),
(2), (4) Date: Oct. 15, 2008

(87) PCT Pub. No.: WO2006/006195
PCT Pub. Date: Jan. 19, 2006

(65) Prior Publication Data
US 2009/0053151 A1 Feb. 26, 2009

(30) Foreign Application Priority Data
Jul. 13, 2004 (IT) .............................. RM2004A0349

(51) Int. Cl.
*A61K 38/04* (2006.01)
*A01N 37/18* (2006.01)
(52) U.S. Cl. ........ 530/328; 424/401; 424/404; 424/439; 424/49; 514/2.3
(58) Field of Classification Search .................. None
See application file for complete search history.

(56) References Cited

U.S. PATENT DOCUMENTS
6,559,281 B1 5/2003 Jaynes

FOREIGN PATENT DOCUMENTS
WO WO 2006/006195 A1 1/2006

OTHER PUBLICATIONS

Tam et al (European Journal of Biochemistry, 269(3):923-32, 2002).*
Venter, et al., "Reagents and kits, such as nucleic acid arrays, for detecting the expression of over 10,000 Drosophilia genes . . . ", XP002349748 from STN Database 2002:173240.
Homburger Sheila Akiko, et al., URL:http://seqdata.uspto.gov/?pageRequest=viewSequence&docID=06703491&seqID=42064> the whole document & US 6 703 491 B1, Mar. 9, 2004.
Palenik, et al., "The genome of a motile marine Synechococcus," Nature vol. 424, No. 6952, pp. 1037-1042, Aug. 28, 2003 (XP002349749 from EBI Database Q7U7P8).
Pini, et al., "Antimicrobial activity of novel dendrimeric peptides obtained by phage display selection . . . ," Antimicrobial Agents and Chemotherapy, vol. 49, No. 7, Jul. 2005.
Boman, Hans G., "Peptide Antibiotics and Their Role in Innate Immunity," Annu. REv. Immunol., 13:61-92. 1995.
Bracci, Luisa, et al., "Synthetic Peptides in the Form of Dendrimers Become Resistant to Protease Activity," The Journal of Biological Chemistry, vol. 278, No. 47, Issue of Nov. 21, pp. 46590-46595. 2003.
Hancock, Robert E.W., "Peptide Antibiotics," The Lancet, vol. 349. Feb. 8, 1997.
Hancock, Robert E.W., et al., "Cationic Peptides: A New Source of Antibiotics," Tibtech, vol. 16. Feb. 1998.
Houghten, Richard A., et al., "Generation and Use of Synthetic Peptide Combinatorial Libraries for Basic Research and Drug Discovery," Nature, vol. 354. Nov. 7, 1991.
Lozzi, Luisa, et al., "Rational Design and Molecular Diversity for the Construction of Anti-α-Bungarotoxin Antidotes with High Affinity and in Vivo Efficiency," Chemistry & Biology, vol. 10, pp. 411-417. May 2003.
Shai, Yechiel, "Mechanism of the Binding, Insertion and Destabilization of Phospholipid Bilayer Membranes by β-helical Antimicrobial and Cell Non-Selective Membrane-Lytic Peptides," Biochimica et Biophysica Acta 1462, pp. 55-70. 1999.
Tam, James P., "Synthetic Peptide Vaccine Design: Synthesis and Properties of A High-Density Multiple Antigenic Peptide System," Proc. Natl. Acad. Sci., vol. 85, pp. 5409-5413. Aug. 1988.
Zasloff, Michael, "Antimicrobial Peptides of Multicellular Organisms," Nature, vol. 415. Jan. 2002.

* cited by examiner

*Primary Examiner* — Patricia A Duffy
(74) *Attorney, Agent, or Firm* — Lucas & Mercanti, LLP

(57) ABSTRACT

Antibacterial peptides and their multimeric analogues, with a wide range of action and low haemolytic activity are described. In particular, the peptide molecules exhibit a high antimicrobial activity against numerous bacterial species, with reduced cytotoxicity and a low haemolysis rate. The molecules of the invention are advantageously usable as therapeutic agents and coadjutants against infections caused by strains that are resistant to common antibiotics.

12 Claims, 13 Drawing Sheets

|  | Number of colonies | | |
|---|---|---|---|
|  | 1 hr | 48 hrs | 72 hrs |
| M1 | 6 | 172 | 1300 |
| Control | 3500 | 2000 | 2400 |

| | Number of colonies | | | |
|---|---|---|---|---|
| | 1 hr | 24 hrs | 48 hrs | 144 hrs |
| M4 0.5mg/mL | 1 | 4 | 10 | 0 |
| M5 0.5mg/mL | 0 | 0 | 0 | 0 |
| M6 0.5mg/mL | 0 | 0 | 0 | 0 |
| Control | 1600 | 1600 | 1600 | 1600 |

ANTIBACTERIAL PEPTIDES AND ANALOGUES THEREOF

INTRODUCTION

The present invention relates to antibacterial peptides and their multimeric analogues, with wide range of action and low haemolytic activity. In particular, the invention relates to peptide molecules that exhibit a high antimicrobial activity against numerous bacterial species, with reduced cytotoxicity and a low haemolysis rate. The molecules of the invention are advantageously usable as therapeutic agents and coadjutants against infections caused by strains that are resistant to common antibiotics.

The peptides of the invention are in the form of synthetic and/or recombinant peptides, linear and multimerised in any chemical, physical and/or biological form which function as antibacterial agents with broad spectrum.

Antimicrobial peptides are an important component of the innate defences of many living species and they constitute the first line of defence of the immune system against infections, even before antibody and/or cell-mediated responses are fully activated.

At present, more than 800 natural antimicrobial peptides can be counted, and many others have been prepared synthetically.

Some peptides derived from natural sequences are undergoing pharmaceutical development (1).

Natural antimicrobial peptides constitute a numerous and heterogeneous group both in terms of composition and amino acid length. The most widely known natural antimicrobial peptides are cecropin, magainins, tachyplesin, protegrin, indolicidin, defensin and buforin. Their length generally ranges from 12 to 35 amino acids and they have a wide variety of secondary structures. Based on their conformational properties, peptides have been classified in five categories (2):
1. With alpha helix conformation: cecropins (3).
2. Constituted by the predominance of one or two specific residues, such as tryptophan for indolicidin (4) or arginine and proline for peptide PR39 (5).
3. Containing a disulphide bridge: bactenicin (6).
4. Containing multiple disulphide bridges which lead to the formation of relatively rigid beta sheets: defensins (7).
5. Polypeptide derivatives with greater dimensions, known for other biological functions, such as peptides derived from the GIP (gastric inhibitory peptide) (8).

Regardless of the secondary structure exhibited by the antimicrobial peptides, a characteristic they share is the amphipathic nature, due to the ability to adopt a conformation in which groups of hydrophobic amino acids and of positively charged amino acids are spatially organised in distinct regions. The cationic as well as hydrophobic nature of antimicrobial peptides enables them to selectively interact with the membrane of bacterial cells, composed mainly of negatively charged phospholipids. Although the action mechanism of antimicrobial peptides has not yet been fully explained, a model has been proposed that explains the activity of most of these compounds, known as the Shai-Matsuzaki-Huang (SMH) (9, 10, 11) model. The model proposes the interaction of the peptide with the external membrane (carpeting), followed by an alteration in the structure of the membrane itself, due to the displacement of lipidic molecules with the formation of toroidal pores that allow the passage and, in some cases, the diffusion of the peptide towards intracellular targets. A certain number of peptides have been proven to be able to bind the lipopolysaccharide (LPS) (12) with a certain affinity exercising both a destabilising effect on the outer membrane of Gram negative bacteria, and a detoxifying effect.

Therefore, most peptides with antimicrobial activity, apparently act according to a non-specific mechanism as confirmed by the fact that the D and L enantiomers of cecropin remain equally active (13, 14, 15). This fact would lead to exclude the hypothesis that there may be a stereo-specific interaction of the receptor-ligand type, and would explain the wide range of action of natural peptides against Gram negative and Gram positive bacteria, yeasts and fungi, tumour cells, and some viruses (HIV and Herpes Simplex).

In general, peptides that act at membrane level according to the SMH model are effective against micro-organisms at micromolar concentrations (1). However, there are some exceptions, such as nisin, a peptide of 14 amino acids produced by the bacteria of the *Lactococcus* genus, which binds Lipid II, a precursor of the peptidoglycan of the bacterial membrane, with high affinity. The specificity of this interaction would justify the antimicrobic effect of nisin even at nanomolar concentrations (16).

For antimicrobial peptides to be employed in clinical use, the selectivity of the action mechanism is crucial to prevent them from being toxic for the receiving organism. Antimicrobial peptides generally have less affinity for the membrane of the cells of the host organism, which exhibit a different phospholipidic composition from bacteria and fungi. In particular, bilayers enriched in the zwitterionic phospholipids phosphatidylethanolamine, phosphatidylcholine, or sphingomyelin, commonly found in mammalian cytoplasmic membranes, are generally neutral in net charge (9, 11). Moreover, the presence of cholesterol in the target membrane in general reduces the activity of antimicrobial peptides, due either to stabilization of the lipid bilayer or to interactions between cholesterol and the peptide.

The interest of antimicrobial peptides in clinical use is also related to their mechanism of action, which is potentially able to overcome the urgent problem of resistance to antibiotics. Since the target of antimicrobial peptides is the bacterial membrane, a microbe would have to redesign its membrane, changing the composition and/or organization of its lipids, which is probably a 'costly' solution for most microbial species. Antimicrobial peptides, therefore, are the best candidates to become a new class of wide range antibiotic drugs.

However, some problems related to their in vivo use have yet to be solved, since some of these natural peptides (e.g. mellitin) are particularly haemolytic or exhibit a short half-life due to their low stability in blood because of the presence of protease and in particular of peptidase.

The use of combinatorial library is a modern, efficient method that allows to select new "lead compounds" with antibiotic activity, selecting them from an extremely high number of different potential peptides. The greater the complexity of the peptide library, the higher the possibility of identifying highly effective compounds. For this purpose, three different combinatorial libraries can be used, but the person skilled in the art may identify other reference sources for peptides:
1. Peptide libraries obtained by chemical synthesis on solid phase (17).
2. Peptide libraries obtained by chemical synthesis as a mixture of free compounds in solution (18).
3. Peptide libraries expressed on the surface of filament phages (19).

The combination of the approach 3 and the chemical synthesis of peptides in solid phase has allowed the discovery of the molecules of the present invention.

DESCRIPTION OF THE INVENTION

The authors of the invention have identified peptide sequences capable of interacting with the bacterial membrane and hence potentially to perform an antibiotic effect according to the mechanism proposed for natural antimicrobial peptides.

Therefore, the object of the present invention is an antibacterial peptide having one of the following amino acid sequences from the amino to the carboxylic terminal: QEKIRVRLSA [SEQ ID NO: 1], QAKIRVRLSA [SEQ ID NO: 2], QKKIRVRLSA [SEQ ID NO: 4], KIRVRLSA [SEQ ID NO: 3] or any derivative thereof, wherein one amino acid residue is replaced by an alanine residue or wherein one positively charged amino acid is replaced by another positively charged amino acid.

Preferably the peptide has one of the following amino acid sequences from the amino to
the carboxylic terminal: AKKIRVRLSA [SEQ ID NO: 5], QAKIRVRLSA [SEQ ID NO: 2], QKAIRVRLSA [SEQ ID NO: 6], QKKARVRLSA [SEQ ID NO: 7], QKKIAVRLSA [SEQ ID NO: 8], QKKIRARLSA [SEQ ID NO: 9], QKKIRVALSA [SEQ ID NO: 10], QKKIRVRASA [SEQ ID NO: 11], QKKIRVRLAA [SEQ ID NO: 12]. More preferably the peptide has the amino acid sequence QKAIRVRLSA [SEQ ID NO: 6]. Alternatively the peptide has one of the following amino acid sequence: QRKIRVRLSA [SEQ ID NO: 13], QKRIRVRLSA [SEQ ID NO: 14], QRRIRVRLSA [SEQ ID NO: 15].

In an embodiment the peptide is of linear form, preferably multimerised on a skeleton of polyacrylamide, on a skeleton of dextrane units or on a skeleton of ethylene glycol units.

In a preferred embodiment the peptide is in the form of Multiple Antigenic Peptides (MAP), having the following formula:

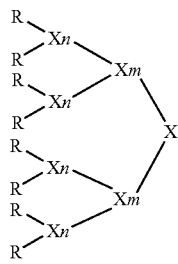

in which R is the peptide as claimed in claim 1-4; X is a trifunctional molecule; m=0 or 1; n=0, if m=0; n=0 or 1, if m=1.

Preferably X is an amino acid having at least two functional aminic groups, more preferably X is lysine, ornithine, norlysine or amino alanine.

Alternatively X is aspartic acid or glutamic acid.

Alternatively X is propylene glycol, succinic acid, diisocyanates or diamines.

The peptides of the invention are used for the preparation of a medicament with antibacterial activity. The person skilled in the art will choose the appropriate form of administration and dosage, selecting suitable dilutants, coadjutants and/or excipients. Preferred forms are eyewashes, mouthwashes, solutions for topical use.

The peptides of the invention are also used for the preparation of disinfectant and/or detergent products with antibacterial activity.

The peptides of the invention are also used as preservatives for the preparation of food products and/or of cosmetic products and/or of homeopathic products.

RESULTS

Selection and Modification of Peptides with Antimicrobial Activity

The authors have produced and used a phage library of peptides with random sequence at high variability (~$10^{10}$), in which each peptide is formed by 10 amino acid residues. The selection of the specific ligands was made by incubating the entire library with a solution of whole cells of *E. coli*, strain TG1 (at the $OD_{600}$ of about 0.1) in PBS. After 1 hour of incubation, the bacteria were centrifuged and the supernatant was eliminated. Several washings with PBS-Tween followed by centrifugation and elimination of the supernatant were performed to eliminate all the phages which bind aspecifically to the bacterial surface or which expose peptides with low affinity for the bacterial membrane. A glycine solution (0.2 M, pH 2.2) was added to the test tube containing bacteria and specific phages for 10 minutes, in order to determine the detachment of the phages bound to the membrane. After further centrifugation, the supernatant containing the eluted phages was collected. The selected phages were amplified in bacterial cells and used for two more rounds of selection. At the end of the process, the presence of specific phages was verified by ELISA assay. DNA analysis revealed the predominance of a sequence with potential amphipathic properties and positive net charge: QEKIRVRLSA [SEQ ID NO: 1] (L1). The letters are the acronyms of the aminoacids in accordance with IUPAC-IUB nomenclature.

It should be noted that the isolated sequence has the typical pattern of antimicrobic peptides which is characterised by alternating hydrophobic residues and positively charged residues (K and R). The peptide in question was synthesised in linear form and in tetrabranched multimeric form MAP (Multiple Antigen Peptide) (20), in which four identical peptides are bonded to a lysine core (U.S. Pat. No. 5,229,490). It has been shown that MAP multimeric forms, due to the presence of 4 peptides in the same molecule, displayed increased antimicrobial activity. In addition, MAP multimeric form constitute peptides that are more resistant to the peptidase activity of blood, compared to their homologous linear peptides (22, 23), enabling to overcome the bottleneck of the development and in vivo use of new peptide drugs.

Figure 6:
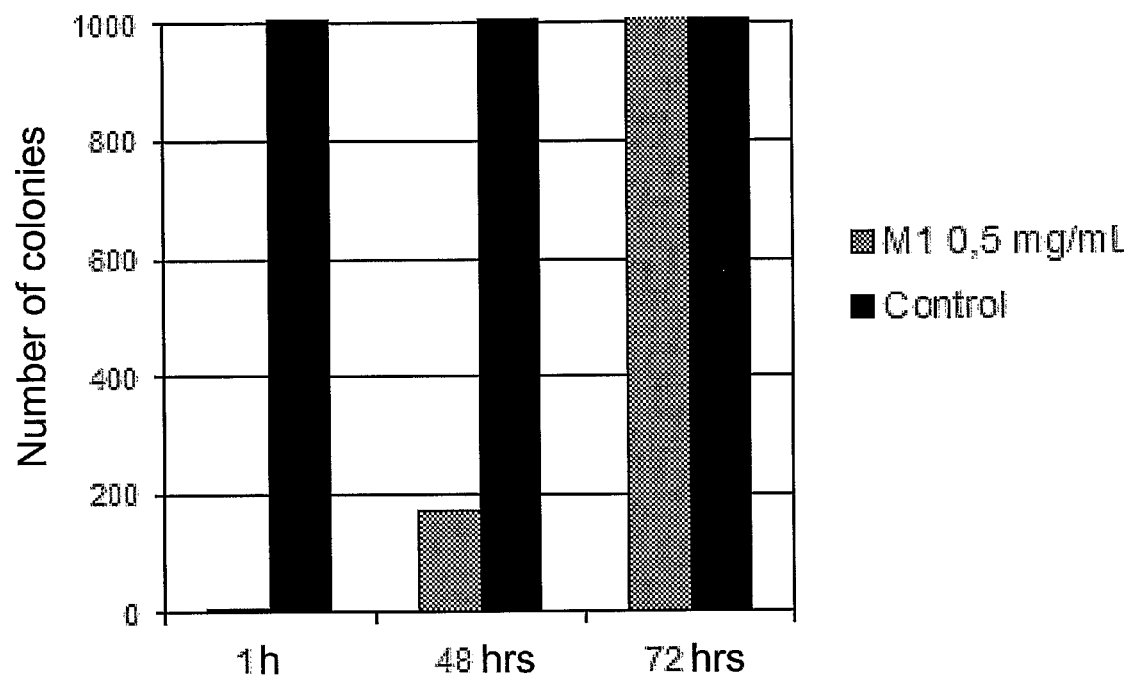
FIG. 6. Stability of M1 peptide in solution. Time course of antibacterial activity of M1 on *E. coli* strain TG1. MAP M1 peptide was dissolved in PBS at a concentration of 0.5 mg/ml and bactericide activity was measured 1, 48 and 72 hours after re-suspension in PBS.

M1 efficacy showed a drop in activity over time (FIG. 6), once resuspended in solution. Mass spectrometry analysis performed on the peptide at various time points indicated that the loss of activity was probably due to amide bond formation between the carboxylic group of the glutamic acid (E) in position two and the adjacent aminic group of lysine (K), with the elimination of an $H_2O$ molecule (not shown).

In order to potentially improve the characteristics of the original sequence QEKIRVRLSA [SEQ ID NO: 1], three peptides were synthesised, starting from the original sequence and replacing glutamic acid (E) with a hydrophobic residue such as alanine (A), or with a positively charged residue such as lysine (K), and lastly performing a deletion of the first two aminoacids at the amino-terminal end. The sequences of the MAP peptides thus modified are QAKIRVRLSA [SEQ ID NO: 2] (M4), QKKIRVRLSA [SEQ ID NO: 4](M6), KIRVRLSA [SEQ ID NO: 3] (M5) (Table 1).

TABLE 1

Peptide sequence of L1, L4, L5, L6

| Peptide sequence | chemical form | abbreviation |
|---|---|---|
| QEKIRVRLSA [SEQ ID NO: 1] | Linear and MAP | L1 and M1 |
| QAKIRVRLSA [SEQ ID NO: 2] | Linear and MAP | L4 and M4 |
| KIRVRLSA [SEQ ID NO: 3] | Linear and MAP | L5 and M5 |
| QKKIRVRLSA [SEQ ID NO: 4] | Linear and MAP | L6 and M6 |

Figure 8:
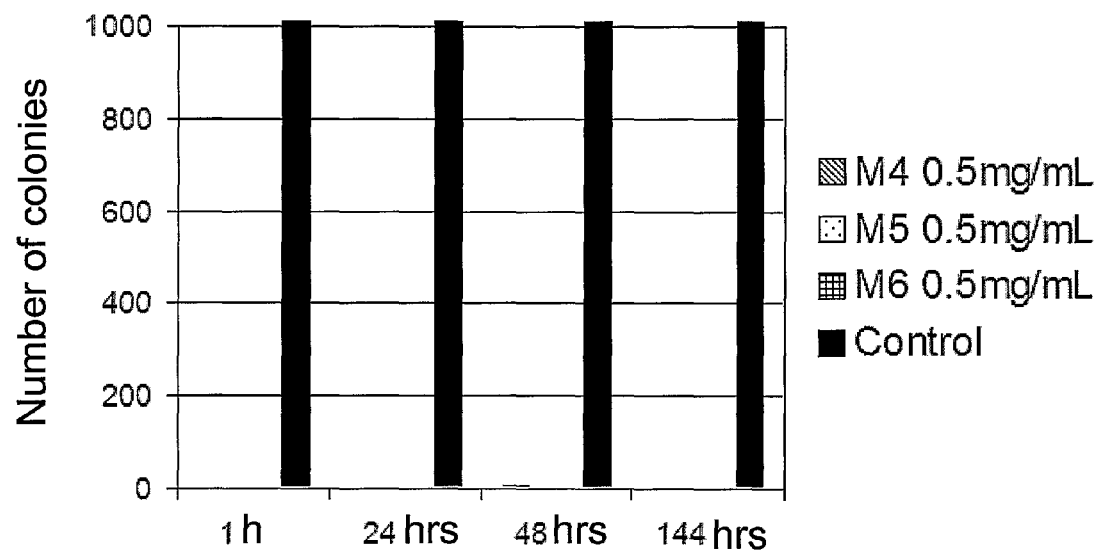
FIG. 8. Stability of M4, M5 and M6 peptides in solution. Time course of antibacterial activity of M4, M5 and M6 on *E. coli* strain TG1. M4, M5 and M6 peptides were dissolved in PBS at a concentration of 0.5 mg/ml and bactericide activity was measured 1, 48 and 144 hours after re-suspension in PBS.

The bactericidal activity of M4, M5 and M6 was stable over time (up to 144 hours after solubilization, FIG. 8).

Antimicrobial Activity

Figure 1:
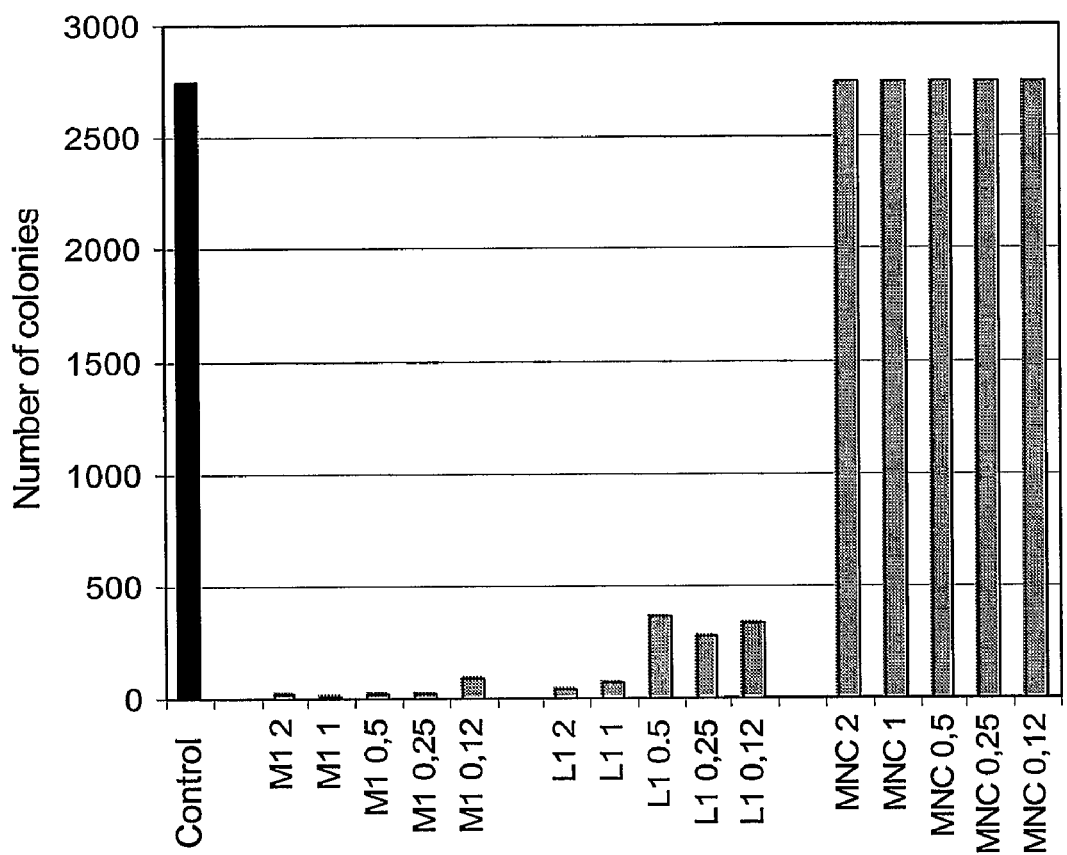
FIG. 1. Antibacterial activity of L 1 and M1 on *E. coli* (TG1 strain) compared to non correlated MAP (MNC) used as negative control. The effect on bacterial growth was assessed at various concentrations (2-0.12 mg/mL). M1 and L1 inhibited significantly *E. coli* growth while MNC, as expected, exhibited no antibacterial activity.

The antimicrobic activity of the peptides in linear form (L1, L4, L5, L6) and in MAP form (M1, M4, M5, M6) was assayed on the TG1 strain of *E. coli*. The peptides were incubated at various concentrations (2-1-0.5-0.25-0.12 mg/ml) with cells of *E. coli* ($OD_{600}$=0.2) for about 1 hour at 37° C. Subsequently, the cells were plated on agar at dilution such to allow counting of individual colonies. The antimicrobic activity of the synthesised peptide L 1 and M1 is shown FIG. 1 and is compared to a non correlated MAP peptide (MNC) used as negative control. While the non correlated MAP peptide exhibits no activity on bacterial colony growth, the authors observed that the inhibitory activity of the peptide M1 in dendrimeric form is greater than the one of the linear peptide, L1. This demonstrates that the efficacy of the antibacterial peptide depends exclusively on its primary sequence.

Figure 2:
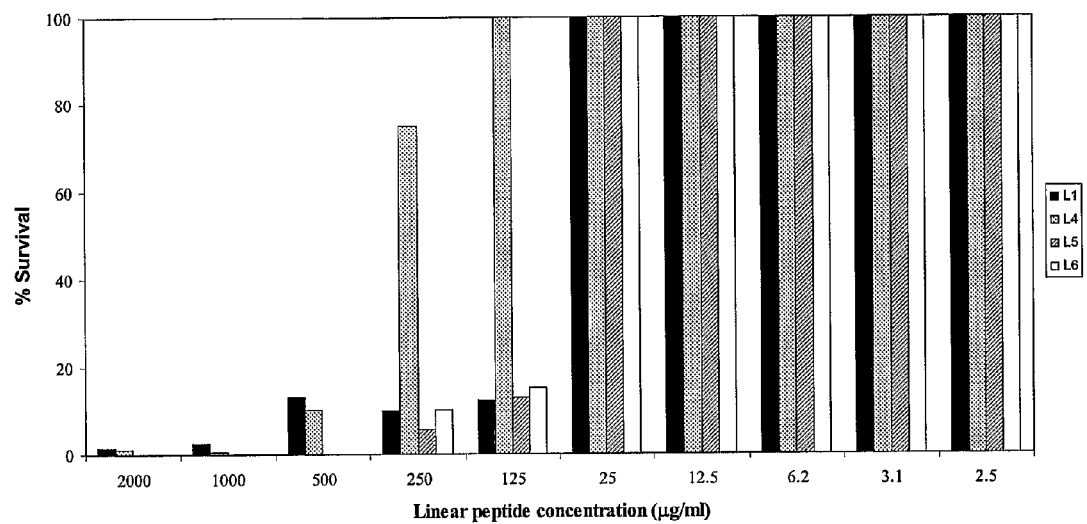
FIG. 2. Antibacterial activity of (A) monomeric linear peptides L1 (■), L4 (■), L5 (■) and L6 (□) and (B) tetrabranched MAP4 form M1 (■), M4 (■), M5 (■) and M6 (□). Experiments were performed incubating *E. coli* TG1 cells ($8 \times 10^7$ CFU/ml) with the indicated amounts of peptide. The survival percentage is the number of living colonies with respect to the number of colonies in controls without peptides.
Figure 2:
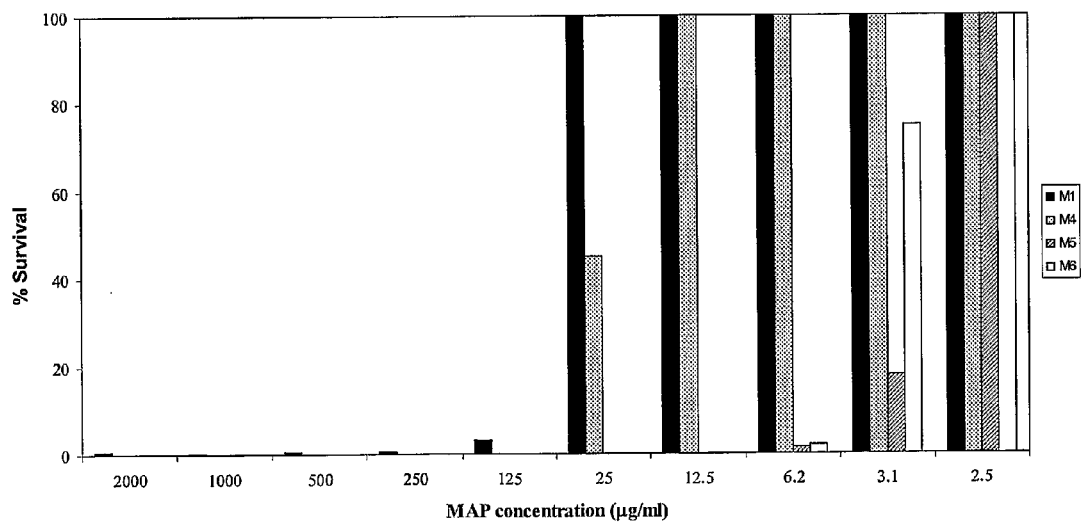

The survival percentage (number of living colonies with respect to the number of colonies in control conditions without peptide) after treatment with the original peptide and with the modified peptides was determined (FIG. 2). The authors observed that in dendrimeric MAP4 form the peptides M1, M4, M5 and M6 presented a greater activity than their linear counterparts (L1, L4, L5 and L6) (FIGS. 2A and B). The modified peptides (M4, M5, M6) showed good antibacterial activity. Notably, M5 and M6 (which contain one and two additional positive charges, respectively) prevented TG1 *E. coli* colony growth at concentrations down to 6.25 μg/ml, whereas M1 and M4 appeared less effective at the same concentrations (FIG. 2B).

Minimum inhibitory concentrations (MIC) of M4, M5 and M6 were determined for the reference strains: *S. aureus* ATCC 25923, *E. coli* ATCC 25922, *Chryseobacterium meningosepticum* CCUG 4310 and *P. aeruginosa* ATCC 27853, as well as for a number of recent clinical isolates (including multidrug-resistant ones) of various species (Table 2).

TABLE 2

MICs of antimicrobial peptides for various Gram negative and Gram positive bacteria.

| Species and strain | Relevant Features[a] | MIC (Molarity) of: M4 | M5 | M6 |
|---|---|---|---|---|
| Escherichia coli ATCC 25922 | Reference strain | $2.6 \times 10^{-5}$ | $3.8 \times 10^{-6}$ | $1.5 \times 10^{-6}$ |
| Escherichia coli W99FI0077 | FQ$^R$ ESC$^R$ (ESBL/SHV type) | $3.2 \times 10^{-6}$ | $3.1 \times 10^{-5}$ | $1.5 \times 10^{-6}$ |
| Escherichia coli W03BG0025 | FQ$^R$ AG$^R$ ESC$^R$ (ESBL/CTX-M-15) | ND[b] | ND | $1.5 \times 10^{-6}$ |
| Escherichia coli W03NO0013 | FQ$^R$ ESC$^R$ (ESBL/CTX-M-1) | ND | ND | $1.5 \times 10^{-6}$ |
| Pseudomonas aeruginosa ATCC27853 | Reference strain | $6.4 \times 10^{-6}$ | $3.8 \times 10^{-6}$ | $7.6 \times 10^{-7}$ |
| Pseudomonas aeruginosa 885149 | FQ$^R$ AG$^R$ ESC$^R$CP$^R$ (MBL/IMP-13) | $1.3 \times 10^{-5}$ | $7.6 \times 10^{-6}$ | $1.5 \times 10^{-6}$ |
| Pseudomonas aeruginosa 891 | FQ$^R$ AG$^R$ ESC$^R$ CP$^R$(MBL/VIM-2) | $1.3 \times 10^{-5}$ | $3.8 \times 10^{-6}$ | $1.5 \times 10^{-6}$ |
| Pseudomonas aeruginosa VA463/98 | FQ$^R$ AG$^R$ ESC$^R$ (ESBL/PER-1) | ND | ND | $7.6 \times 10^{-7}$ |
| Klebsiella pneumoniae W99FI0057 | ESC$^R$ (ESBL/SHV type) | $1.3 \times 10^{-5}$ | $>3.1 \times 10^{-5}$ | $7.6 \times 10^{-7}$ |
| Klebsiella pneumoniae W03NO0078 | ESC$^R$ (ESBL/CTX-M-1) | ND | ND | $3.0 \times 10^{-6}$ |
| Klebsiella pneumoniae W03BG0019 | AG$^R$ ESC$^R$ (ESBL/CTX-M-15) | ND | ND | $1.5 \times 10^{-6}$ |
| Klebsiella oxytoca W99FI00049 | ESC$^R$ (ESBL/SHV-12) | ND | ND | $1.2 \times 10^{-5}$ |
| Proteus mirabilis W99FI0089 | FQ$^R$ | ND | ND | $>4.9 \times 10^{-5}$ |
| Proteus mirabilis W03VA1144 | FQ$^R$ AG$^R$ ESC$^R$ (ESBL/PER-1) | ND | ND | $1.2 \times 10^{-5}$ |
| Enterobacter aerogenes W03BG0067 | AG$^R$ ESC$^R$ (ESBL/SHV-5) | ND | ND | $1.5 \times 10^{-6}$ |
| Enterobacter cloacae W03AN0041 | ESC$^R$ (ESBL/SHV-12) | ND | ND | $7.6 \times 10^{-7}$ |
| Morganella morganii W03VA1342 | FQ$^R$ ESC$^R$ (ESBL/CTX-M-1) | ND | ND | $>4.9 \times 10^{-5}$ |
| Acinetobacter baumannii AB1MG | FQ$^R$ AG$^R$ ESC$^R$ (ESBL/TEM-92) | ND | ND | $3.0 \times 10^{-6}$ |
| Acinetobacter baumannii AB7MG | FQ$^R$ AG$^R$ ESC$^R$ | ND | ND | $6.0 \times 10^{-6}$ |
| Citrobacter freundii W99FI00007 | ESC$^R$ (ESBL/SHV-12) | ND | ND | $3.0 \times 10^{-6}$ |
| Chryseobacterium meningosepticum CCUG4310 | Reference strain | ND | ND | $>4.9 \times 10^{-5}$ |
| Burkholderia cepacia SMC71 | FQ$^R$ AG$^R$ ESC$^R$ | ND | ND | $1.2 \times 10^{-5}$ |
| Serratia marcescens W99FI0111 | FQ$^R$ AG$^R$ ESC$^R$ (ESBL/SHV-5) | ND | ND | $>4.9 \times 10^{-5}$ |
| Stenotrophomonas maltophilia PT4/99 | Wild-type profile | ND | ND | $>4.9 \times 10^{-5}$ |
| Providencia stuartii W03FI0001 | AG$^R$ ESC$^R$(ESBL/PER-1) | ND | ND | $>4.9 \times 10^{-5}$ |
| Staphylococcus aureus ATCC 25923 | Reference strain | $1.3 \times 10^{-5}$ | $3.1 \times 10^{-5}$ | $>4.9 \times 10^{-5}$ |
| Staphylococus aureus MIU-68A | MS | $>2.6 \times 10^{-5}$ | $3.1 \times 10^{-5}$ | $4.9 \times 10^{-5}$ |

Except for reference strains, all other strains were clinical isolates. Relevant resistance phenotypes and known resistance mechanisms are indicated.
FQ$^R$, resistance to fluoroquinolones (ciprofloxacin);
AG$^R$, resistance to aminoglycosides (gentamicin and/or amikacin and/or tobramycin);
ESC$^R$, resistance to extended-spectrum cephalosporins (cefotaxime and/or ceftazidime and/or cefepime);
CP$^R$, resistance to carbapenems (imipenem and/or meropenem);
ESBL, extended-spectrum β-lactamase;
MBL, metallo β-lactamase;
MS, meticillin-susceptible.
ND, not determined.

MIC is defined as the lowest concentration, in an antibiotic dilution range, that inhibits visible bacterial growth. The importance of MIC sensitivity test is based on the principle that in vitro sensitivity provides a predictive indication of the in vivo efficacy of the antibiotic therapy. Values are expressed as molar concentration and compared to MIC values obtained with commercially available antibiotics such as amikacin, ceftriaxone and levofloxacin (Table 3).

TABLE 3

MIC of known antibiotics against reference bacterial species

| Strain | AMIKACIN MIC (Molarity) | CEFTRIAXONE MIC (Molarity) | LEVOFLOXACIN MIC (Molarity) |
|---|---|---|---|
| S. aureus ATCC 25923 | $8.5 \times 10^{-7}$-$6.8 \times 10^{-6}$ | $5.4 \times 10^{-8}$-$2.1 \times 10^{-7}$ | $2.2 \times 10^{-8}$-$1.6 \times 10^{-5}$ |
| E. coli ATCC 25922 | $1.7 \times 10^{-6}$-$6.8 \times 10^{-6}$ | $1.4 \times 10^{-5}$-$1.1 \times 10^{-4}$ | $1.3 \times 10^{-6}$-$1.1 \times 10^{-5}$ |
| P. aeruginosa ATCC 27853 | $1.7 \times 10^{-6}$-$6.8 \times 10^{-6}$ | $1.7 \times 10^{-6}$-$1.4 \times 10^{-5}$ | $1.6 \times 10^{-7}$-$1.3 \times 10^{-6}$ |

From these data, it is readily apparent that the values of MIC for M4, M5 and M6 are low (in the order of $10^{-6}$-$10^{-7}$ M) whereas the best antimicrobic peptides known in the literature reach MIC values of around $10^{-6}$M (0.25-4 μg/mL) (25).

All peptides showed relatively poor activity against *S. aureus*, appearing to be more active against gram-negative bacteria, with M6 being the most active against all species. M6 presented also a good inhibitory activity against *E. coli, Klebsiella pneumoniae, Enterobacter* spp. and *P. aeruginosa*, including clinical isolates showing a multiple-drug resistance phenotype. A somewhat lower activity was observed against *Citrobacter freundii* and *Acinetobacter baumannii*, and even lower activity against *Proteus mirabilis, Morganella morganii, Providencia stuartii, Stenotrophomonas maltophilia, Burkholderia cepacia*, and *Chryseobacterium meningosepticum* (Table 2). Subsequently, the minimal concentration of the M4, M5 and M6 peptides able to kill 99.9% of the original bacterial inoculum (MBC) was evaluated. The MBC was calculated on strains of *E. coli* ATCC 25922 and *P. aeruginosa* ATCC 27853 and it was found to be equal to the calculated values of MIC for the same strains. The equality of the values of MIC and MBC provides the indication that M4, M5 and M6 peptides are bactericidal and not bacteriostatic.

Figure 3:
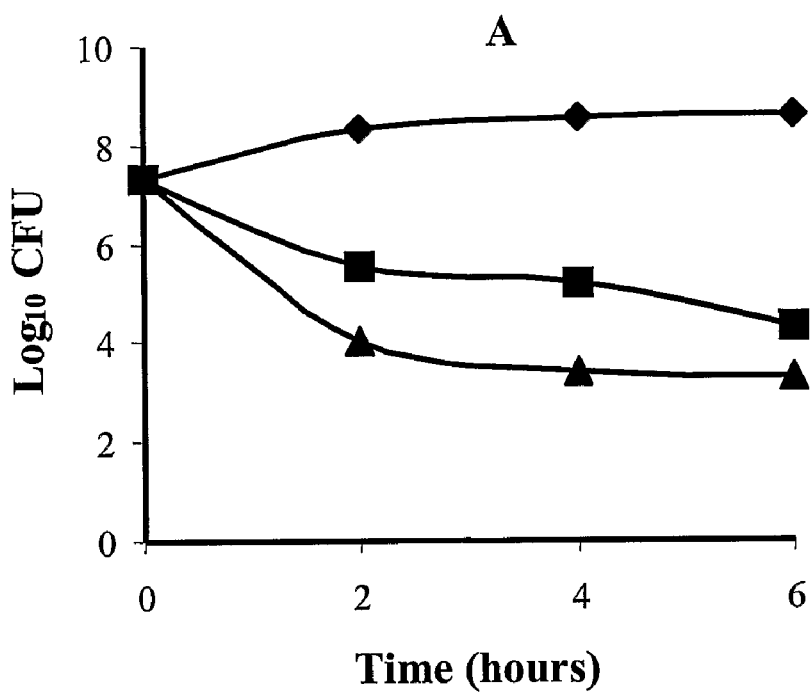
FIG. 3. Time-kill kinetics of M6 against *E. coli* ATCC 25922 (A) and *P. aeruginosa* ATCC 27853 (B). Symbols: ◆, growth control; ■, 2×MIC concentration (16 µg/ml) for *E. coli* ATCC 25922 and 8 µg/ml for *P. aeruginosa* ATCC 27853); ▲, 4×MIC (32 µg/ml) for *E. coli* ATCC 25922 and 16 µg/ml for *P. aeruginosa* ATCC 27853).
Figure 3:
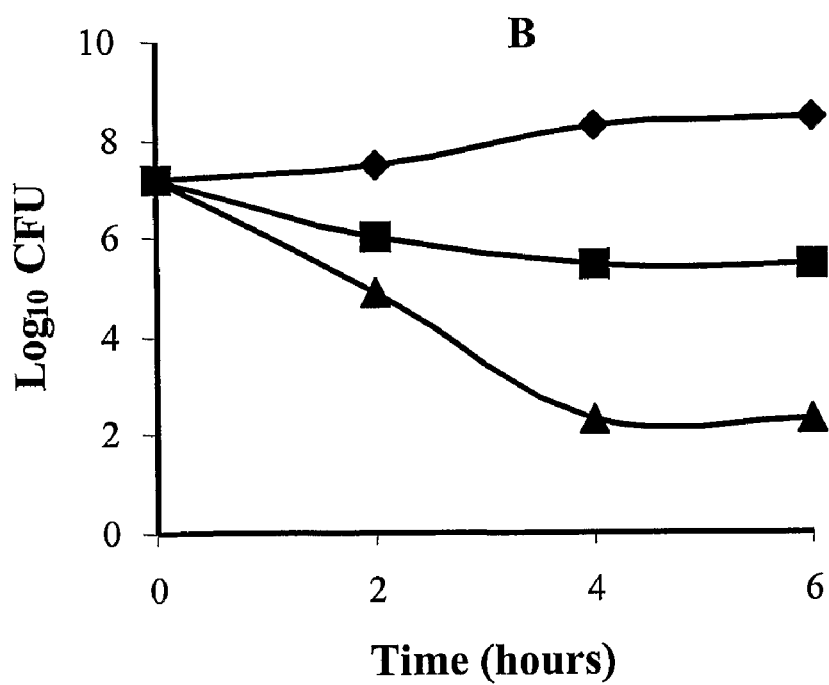

Time-kill experiments demonstrated that M6 exhibited rapid bactericidal activity against *E. coli* ATCC 25922 and *P. aeruginosa* ATCC 27853, reducing an inoculum larger than $10^7$ CFU by >99.9% in 4 h, at a concentration of 16 μg/ml (FIG. 3). Bactericidal activity appeared to be concentration-dependent, especially with *P. aeruginosa*.

Due to their low MIC values, the peptides could be administered at low doses, improving patient compliance, but also the cost-effect ratio of such therapy.

Cytotoxicity

Figure 4:
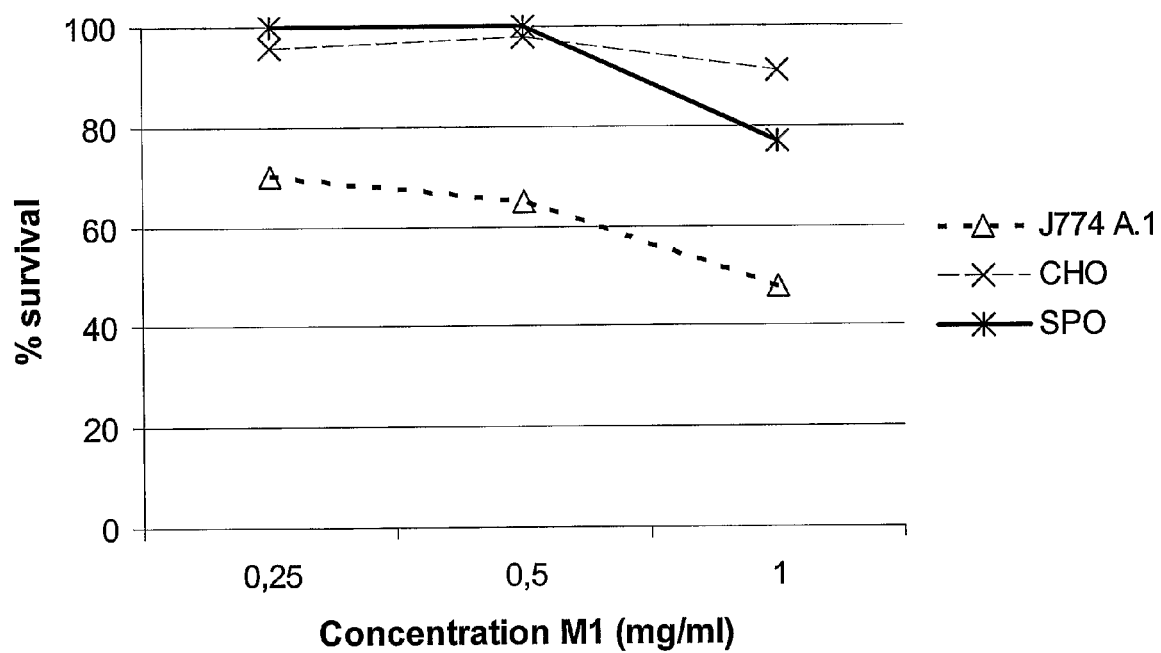
FIG. 4. Cytotoxicity of M1 on J774 A.1, CHO and SPO cells. The figure shows the cytotoxicity of the MAP M1 peptide expressed in terms of percent of survival evaluated on murine macrophage cells (J774 A.1), murine myeloma (SPO) and Chinese hamster ovary epithelium cells (CHO K1) by means of a colorimetric assay (MTT). M1 was added to the various cell lines ($6 \times 10^4$ cells/well) at three different concentrations and incubated for 24 hours at 37° C. Then 100 µl of MTT were added to each well and incubated for 90 min at 37° C. The absorbance values at 595 and 650 nm were measured.

The cytotoxicity of antibacterial MAP peptides was evaluated on different eukaryotic cell lines by a colorimetric assay (MTT). This assay measures the cells' ability to convert a soluble tetrazolium salt into an insoluble precipitate: formazan. The cytotoxicity of M1 was evaluated on murine macrophagic cells (J774 A.1), murine myeloma cells (SPO) and Chinese hamster ovary epithelium cells (CHO K1). As shown FIG. 4, even at high concentrations (1 mg/ml) M1 cytotoxicity on CHO K1 cells and on SPO cells is low (percent survival is 80-90%). By contrast, murine macrophage cells, J774 A1 were found to be more sensitive to M1 (percent survival ~50%).

Figure 5:
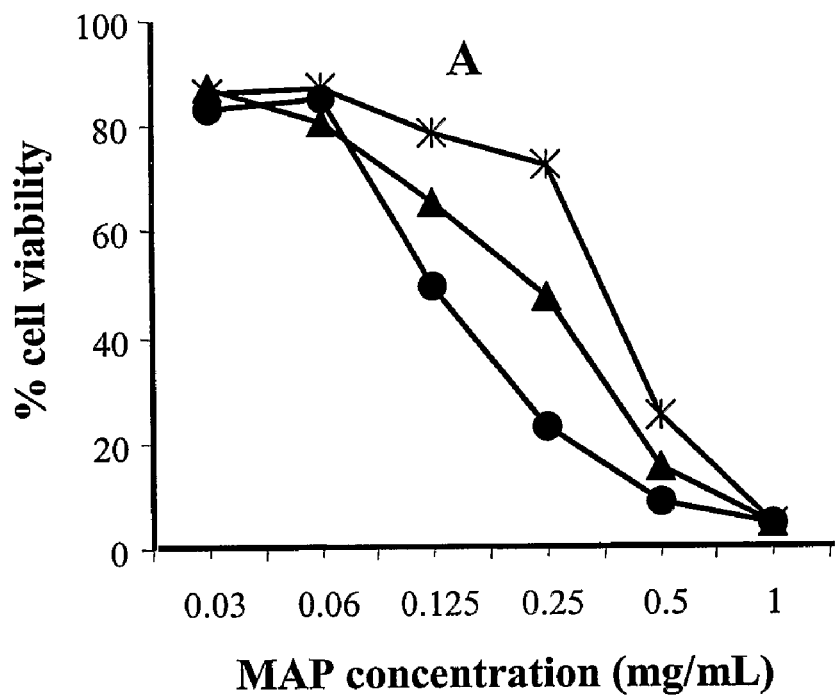
FIG. 5. Toxicity of M4 (*), M5 (▲) and M6 (●) dendrimeric peptides on (A) mouse macrophage cell line J774.A1 and (B) human HaCaT keratinocytes. Cell viability was measured by a colorimetric assay (MTT). Data points represent means of three replicates.
Figure 5:
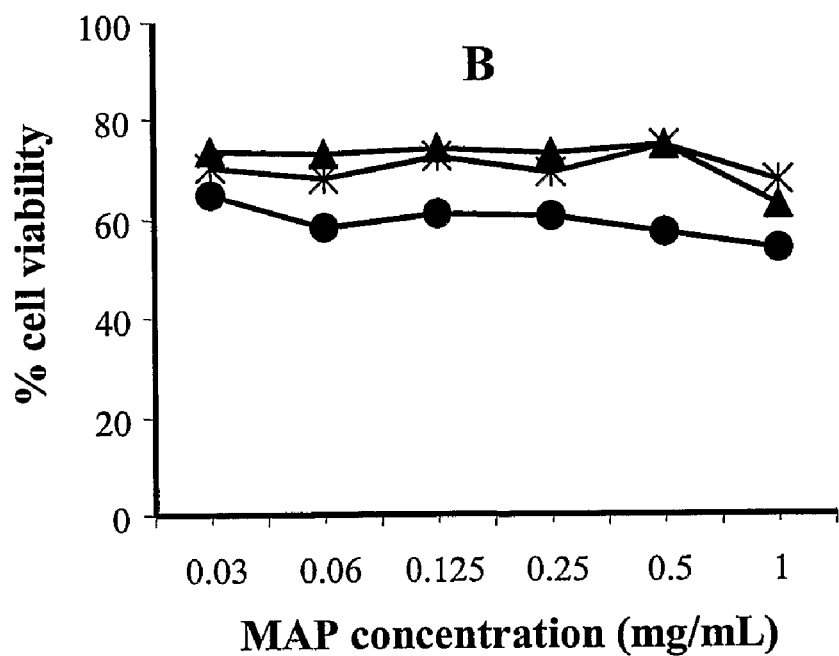

The toxicity of M4, M5 and M6 towards mouse macrophage cells J774.A1 was also tested by MTT and is shown in FIG. 5A. Treatment of cells overnight with 30 μg/ml of M4, M5 or M6, did not substantially affect cell viability, whereas a drop in cell viability was evident after treatment with peptide M4 at concentrations of 250 μg/ml and over, and with peptides M5 and M6 at 125 μg/ml and over. The same dendrimeric peptides showed low toxicity for human keratinocyte HaCaT cells (FIG. 5B) even when used at high concentration (1 mg/ml). Moreover, the effect of M4, M5 and M6 on the *Pichia pastoris* yeast, strain X33, was evaluated. The number of colonies of yeast treated with the three antimicrobial peptides did not differ from the negative control suggesting an absence of toxicity of the peptides on yeast (data not shown).

Peptide Stability in Plasma and Serum

Figure 7:
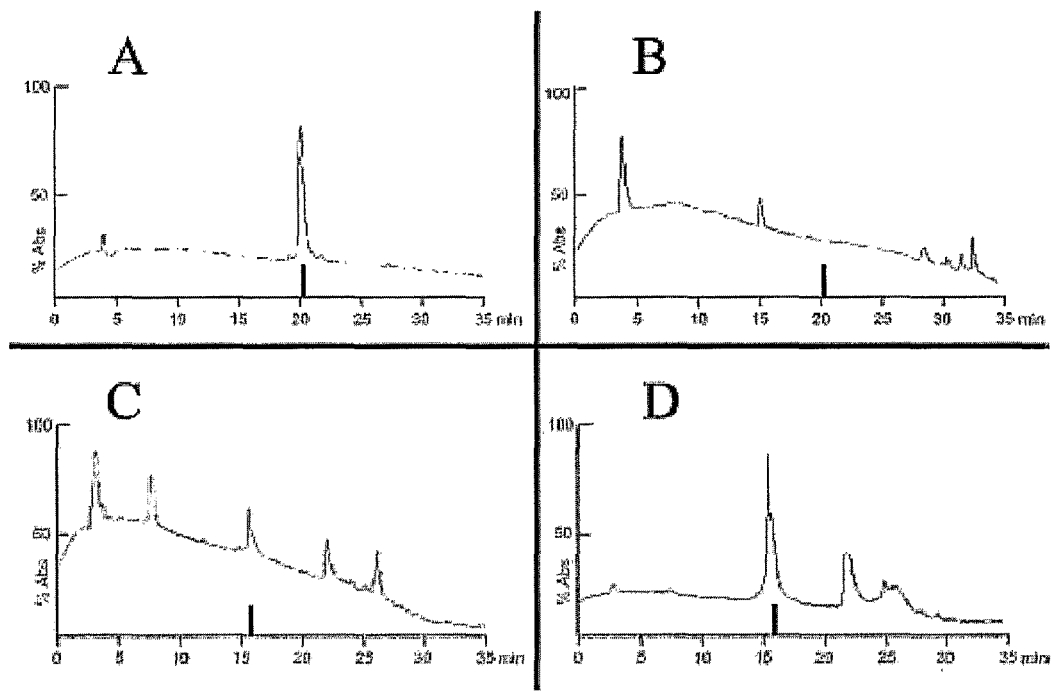
FIG. 7. HPLC profiles of linear (L1) and dendrimeric (M1) peptides in serum. (A) L 1 in serum at 0 h. (B) L 1 after incubation in serum for 2 h: the peptide is no longer detectable. (C) M1 in serum at 0 h. (D) M1 after incubation in serum for 24 h: the peptide is still present. The vertical bar indicates peptide retention time (min). Experiments performed in plasma were comparable.

Since the use of peptides as therapeutic agents is severely limited by their in vivo half-life, the stability to human serum protease of the linear peptide L1 and of the MAP peptides M1, M4, M5 and M6 was evaluated. The peptides were incubated at the concentration of 10 mM with plasma and with human serum for 2 and 24 hours; the samples were subsequently analysed in HPLC on column C18 (see materials and methods) to evaluate the presence of linear and MAP peptide not digested by the protease. The authors observed that monomeric peptide L1 was completely degraded within 2 h in serum, whereas the dendrimeric form of the same peptide (M1) was still detected after 24 h in plasma and serum (FIG. 7, Table 4). Comparable results were obtained with dendrimeric peptides M4, M5 and M6 (Table 4).

TABLE 4

Resistance to serum and plasmatic protease of L1, M1, M4, M5 and M6.

| PEPTIDES | Plasma | | Serum | |
|---|---|---|---|---|
| | 2 h | 24 h | >2 h | 24 h |
| L1 | + | − | − | − |
| M1 | + | + | + | + |
| M4 | + | + | + | + |
| M5 | + | + | + | + |
| M6 | + | + | + | + |

Haemolytic Activity

Figure 9:
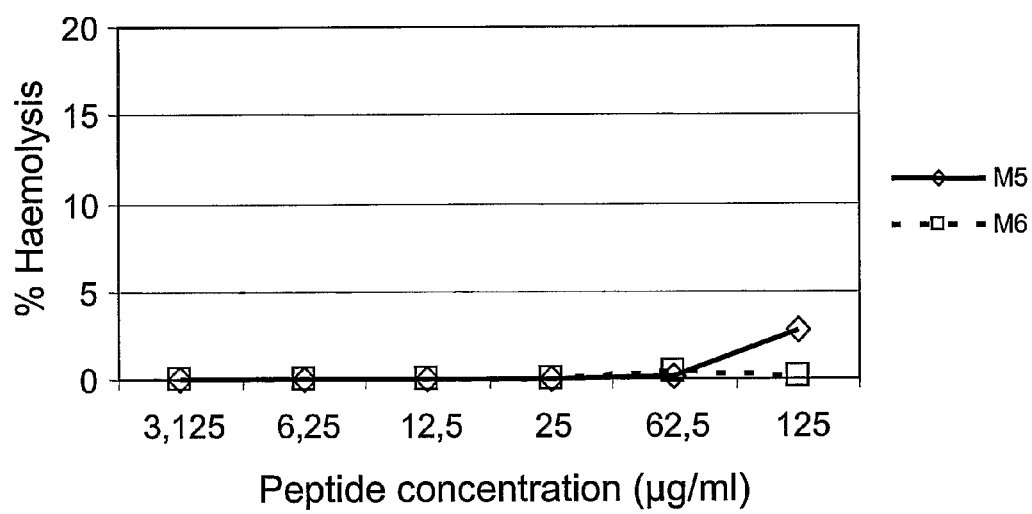
FIG. 9. Effect of M5 and M6 on haemolysis of human erythrocytes. The figures show the haemolytic activity of MAP M5 and M6 peptides on human erythrocytes evaluated by means of erythrocyte osmotic resistance of Parpart method in NaCl. The percentage of haemolysis is calculated by means of a calibration curve obtained by incubating erythrocytes with increasing concentrations of NaCl. After 30 min of incubation, M5 and M6 (at the maximum concentration tested) displayed only a weak haemolytic activity (<5%). After 19 hours of incubation, the haemolysis induced by M6 and M5 at 125 µg/ml is 7% and 19%, respectively. The percentage of haemolysis of untreated blood after 19 hours (control) is very limited (<1).
Figure 9:
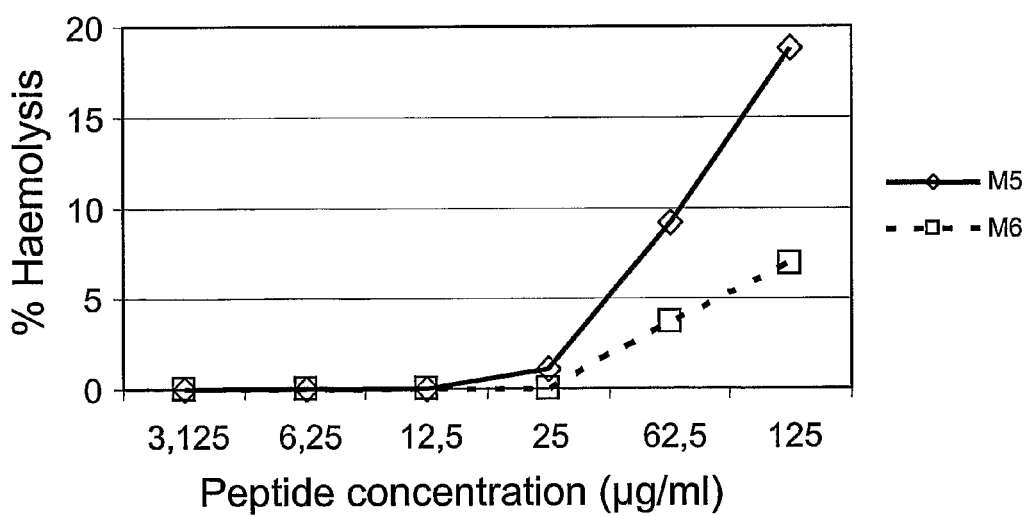

The haemolytic activity of M5 and M6 was also evaluated and is represented FIG. 9. Haemolysis of fresh human erythrocytes was determined at peptide concentrations ranging from 1 to 125 μg/ml. At a concentration of 125 μg/ml all dendrimeric peptides showed very poor haemolytic activity (less than 5%) after an incubation of 30 min. By contrast, after 19 hours of incubation, the haemolysis induced by M6 and M5 at 125 μg/ml is 7% and 19%, respectively. The percentage of haemolysis of untreated blood after 19 hours (control) is very limited (<1%).

Mechanism of Action a) Permeabilization

Figure 10:
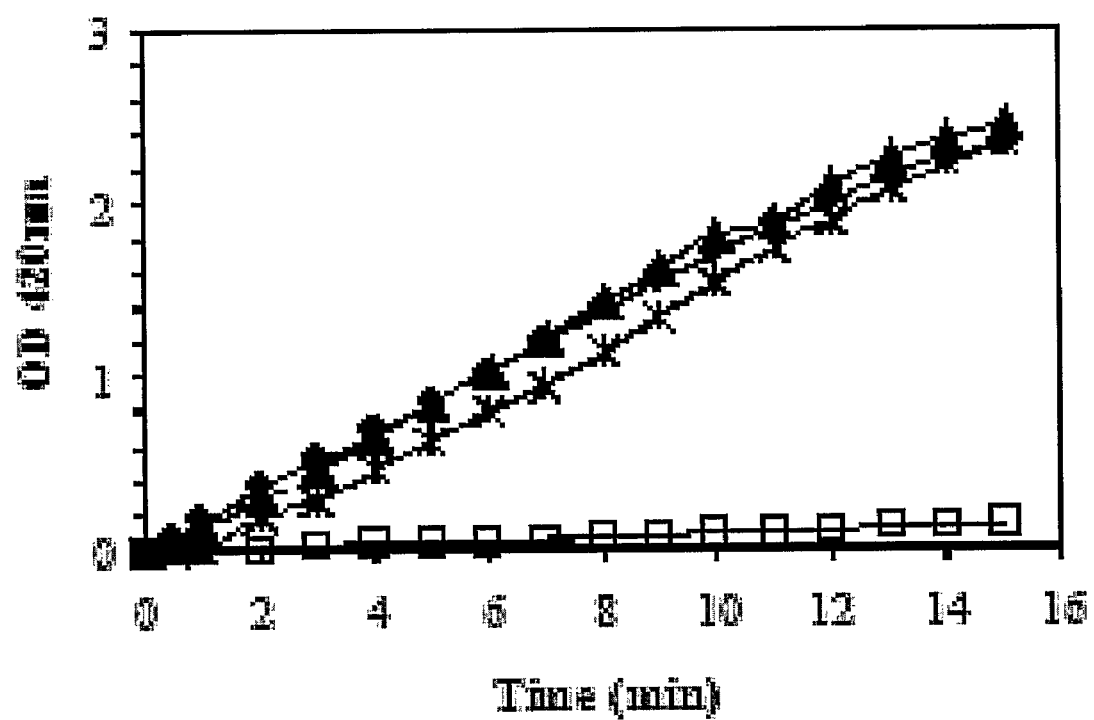
FIG. 10. Kinetics of membrane permeabilization of ML-35 *E. coli* by M4 (*), M5 (▲), M6 (●) and of untreated cells (□). Permeabilization was determined by spectrophotometric recording of hydrolysis of p-nitrophenyl-β-D-galactopyranoside, a substrate for β-galactosidase in the cytosol of bacterial cells. Bacteria were treated with 16 μg/ml of dendrimeric peptides.
Figure 11:
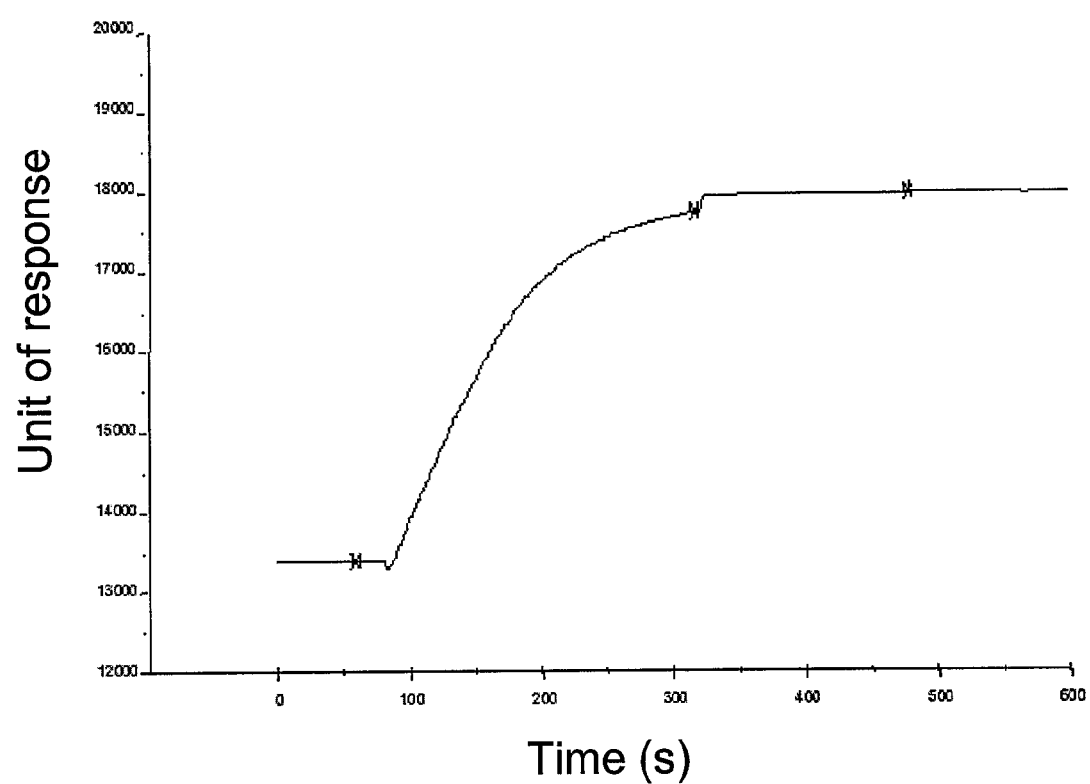
FIG. 11. Binding analysis between MAP M6 peptide and LPS in BIACORE. The figure shows the sensorgram derived from the binding of LPS on MAP M6 immobilised in the dextrane matrix of the BIACORE sensorchip. On the y-axis are shown the Units of Response derived from the binding between LPS and M6 as a function of time expressed in seconds (on the x-axis)

The ability of MAP peptides to perforate the bacterial membrane was evaluated measuring the activity of cytoplasmatic beta-galactosidase (24) in surpernatants of *E. coli* strain ML-35 incubated with the peptide and using p-nitrophenyl-β-D-galactopyranoside (pNPG) as a substrate. pNPG is digested by beta-galactosidase, therefore releasing p-nitrophenolate detectable by spectrophotometric reading at 420 nm (FIG. 10). The permeabilization assays showed that peptides M4, M5 and M6 permeabilize the bacterial inner membrane, unmasking cytoplasmic β-galactosidase in ML-35 *E. coli* permease-negative mutant. The activity of dendrimeric peptides against the inner membrane was evaluated at concentrations of 16, 32 and 64 μg/ml. All dendrimeric peptides permeabilized bacterial inner membrane at 16 μg/ml (FIG. 9). Permeabilization occurred after a lag of less than 1 minute, and the rate of permeabilization depended on peptide concentration (not shown). Moreover, the ability of the M6 MAP peptide to bind the bacterial lipopolysaccharide (LPS) was assayed by Plasmon Surface Resonance in a Biacore 1000 instrument (FIG. 11) using a protocol perfected by the authors (26). The sensorgram shows the rapid binding of M6 to the LPS. This experiment suggests that M6 might have a detoxifying activity.

b) DNA Binding Assay

Figure 12:
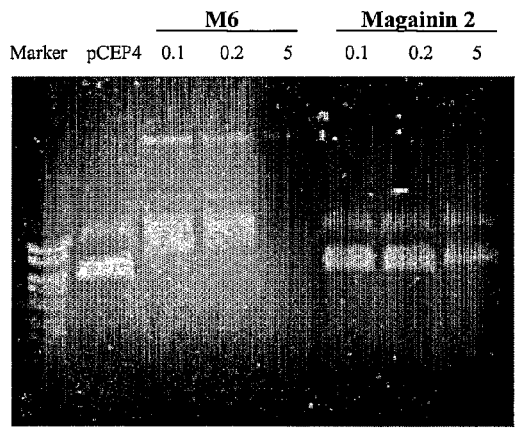
FIG. 12. Gel retardation assay. Binding was assayed by the inhibitory effect of peptides on the migration of DNA. Various amounts of M6 peptide were incubated with 200 ng of *E. coli* plasmid vector pCEP4 at room temperature for 1 h and the reaction mixtures were applied to a 1% (w/v) agarose gel electrophoresis.

In an attempt to clarify the molecular mechanism of action, the authors examined the binding properties on DNA exerted by M6 dendrimeric peptide and magainin 2, an antimicrobial peptide which has a pore-forming activity on the cell membrane. The DNA binding abilities of M6 and magainin 2 were examined by analyzing the electrophoretic mobility of DNA bands at the various weight ratios of peptides to DNA on a 1% (w/v) agarose gel. M6 inhibited the migration of DNA above weight ratio of 0.2 (FIG. 12) while magainin 2 did not suppress the migration of DNA until the weight ratio of 5. This result indicates that M6 binds to DNA at least over 25 times tightly than magainin 2.

c) Confocal Laser-Scanning Microscopy Experiments (CLSM)

Figure 13:
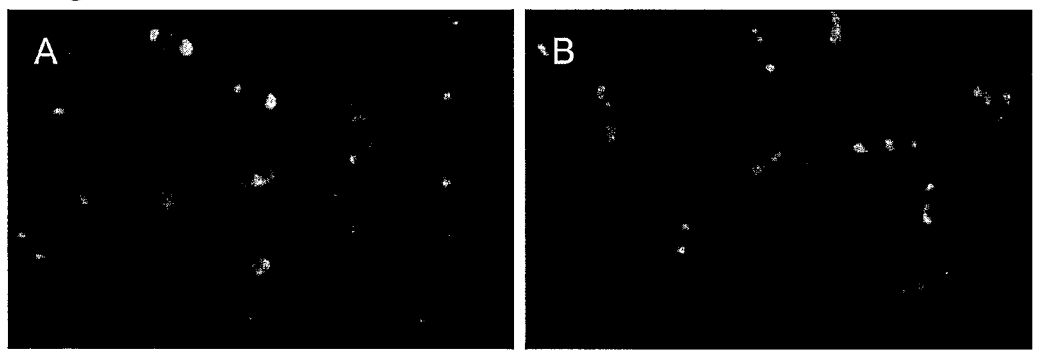
FIG. 13. CLSM image of TG1 *E. coli* cells treated with rhodamine-labelled M6 after (A) 5 min and (B) 240 min of incubation.

CLSM experiments showed that rhodamine-labelled M6 is able to enter the cells within 5 minutes and tends to cluster in discrete patches, often situated at the cell poles, instead of distributing evenly inside the bacteria (FIG. 13). Moreover, there are no significant differences between *E. coli* images taken after 5 (FIG. 13A) or 240 min (FIG. 13B) of incubation with 20 µg/ml M6.

Figure 14:
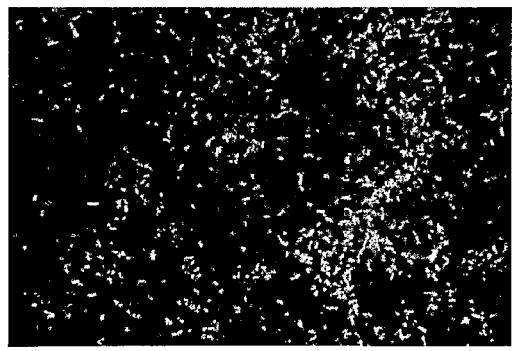
FIG. 14. Bacterial inner-membrane permeation induced by M6 and visualized by FITC fluorescence.
Figure 15:
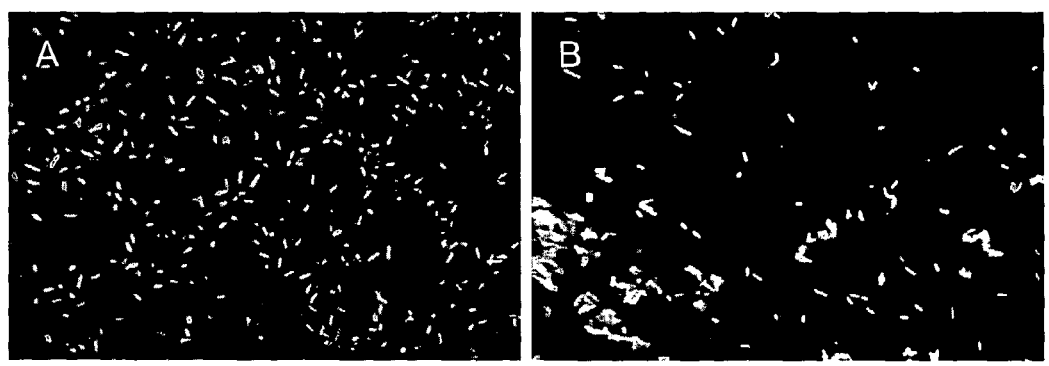
FIG. 15. Detection of membrane-perturbed bacteria using double staining with FITC and PI fluorescent probes. (A) M6 at 5 μg/ml and (B) M6 at 40 μg/ml.

To further visualize the membrane-perturbing activity of M6, the authors used FITC, a low molecular-mass (389.4 Da) green fluorescent probe. FITC was unable to cross the cytoplasmic membrane of control intact cells. Indeed, when *E. coli* TG1 cells were incubated with the probe without pre-treatment with the peptide, no appreciable fluorescent signal was discerned (data not shown). In contrast, FITC was readily accumulated in bacteria after their exposure to 20 µg/ml M6, suggesting that M6 increases the permeability of the bacterial membrane as assessed by CLSM analysis (FIG. 14). The results obtained with the double FITC-PI staining approach are illustrated in FIG. 15. *E. coli* cells were incubated respectively with 5 µg/ml (FIG. 15A), and 40 µg/ml of M6 ((FIG. 15B). The authors observed that microbial cells treated with the highest peptide concentration display an increased membrane permeability to both FITC and PI (FIG. 15B). The lowest concentration of M6 lead to a limited alteration of bacterial membrane (FIG. 15A). Surprisingly, the membrane remained almost impermeable to the smaller dye (FITC, 389.4 Da) but was permeable to the larger dye (PI, 668.4 Da). This finding could be explained by electrostatic interactions of the dye with the bacterial outer membrane: FITC in solution is negatively charged while PI has two positive charges that can promote its uptake. All treated bacteria maintain a typical "stick" shape without losing their nucleic acids content, as manifested by their clear, intense red fluorescence due to propidium iodine binding to DNA.

Improvement in M6 Peptide Activity

In order to identify the critical residues responsible for the antibacterial activity of M6, the sequence of M6 was subjected to "Alanine Scanning". "Alanine Scanning" is a procedure in which every amino acid of the peptide in question is sequentially replaced by an alanine. A mini-library in MAP form of 9 peptides was thereby synthesised (Table 5).

| Peptide sequence | chemical form | abbreviation |
|---|---|---|
| QKKIRVRLSA [SEQ ID NO: 4] | MAP | M6 |
| AKKIRVRLSA [SEQ ID NO: 5] | MAP | M31 |
| QAKIRVRLSA [SEQ ID NO: 2] | MAP | M32 = M4 |
| QKAIRVRLSA [SEQ ID NO: 6] | MAP | M33 |
| QKKARVRLSA [SEQ ID NO: 7] | MAP | M34 |
| QKKIAVRLSA [SEQ ID NO: 8] | MAP | M35 |
| QKKIRARLSA [SEQ ID NO: 9] | MAP | M36 |
| QKKIRVALSA [SEQ ID NO: 10] | MAP | M37 |
| QKKIRVRASA [SEQ ID NO: 11] | MAP | M38 |
| QKKIRVRLAA [SEQ ID NO: 12] | MAP | M39 |

For each MAP peptide, MIC was then calculated on three reference strains: *E. coli* ATCC 25922, *P. aeruginosa* ATCC 27853 (Gram negative) and ATTC25923 (Gram positive)

TABLE 6

MIC values of the peptides derived from Alanine Scanning of M6

| Peptide | *E. coli* ATCC 25922 MIC (Molarity) | *P. aeruginosa* ATCC 27853 MIC (Molarity) | *S. aureus* ATCC 25923 MIC (Molarity) |
|---|---|---|---|
| M6 | $1.5 \times 10^{-6}$ | $7.6 \times 10^{-7}$ | $>4.9 \times 10^{-5}$ |
| M31 | $3.0 \times 10^{-6}$ | $3.0 \times 10^{-6}$ | $>1.2 \times 10^{-5}$ |
| M32 = M4 | $1.2 \times 10^{-5}$ | $6.4 \times 10^{-6}$ | $>1.2 \times 10^{-5}$ |
| M33 | $1.5 \times 10^{-6}$ | $1.5 \times 10^{-6}$ | $>1.2 \times 10^{-5}$ |
| M34 | $>1.2 \times 10^{-5}$ | $1.2 \times 10^{-5}$ | $>1.2 \times 10^{-5}$ |
| M35 | $6.0 \times 10^{-6}$ | $1.5 \times 10^{-6}$ | $>1.2 \times 10^{-5}$ |
| M36 | $>1.2 \times 10^{-5}$ | $>1.2 \times 10^{-5}$ | $>1.2 \times 10^{-5}$ |
| M37 | $3.0 \times 10^{-6}$ | $3.0 \times 10^{-6}$ | $>1.2 \times 10^{-5}$ |
| M38 | $>1.2 \times 10^{-5}$ | $>1.2 \times 10^{-5}$ | $>1.2 \times 10^{-5}$ |
| M39 | $3.0 \times 10^{-6}$ | $3.0 \times 10^{-6}$ | $>1.2 \times 10^{-5}$ |

MIC values obtained for the M6 derivative peptides show that the replacement of alanine with any hydrophobic residue led to a significant increase in MIC reflecting (?) a diminished antimicrobic activity.

From the mini-library, the peptide M33 was identified as particularly active against the Gram negative bacteria, *E. coli* ATCC 25922, and *P. aeruginosa* ATCC 27853 with MIC values, expressed in molarity, of $1.5 \times 10^{-6}$ M for both strains.

Lastly, the effect of replacing the lysines of the M6 peptide with another positively charged aminoacid, arginine (R) was evaluated. Arginine has a more distributed positive charge than lysine, due to the presence of the guanidinium group. The primary amine of lysine and the guanidinium group of arginine appear to interact differently with the bacterial phospholipids (27). For this purpose, 3 peptides in MAP form were synthesised (Table 7).

TABLE 7

Sequence of M6 modified peptides M28, M29 and M30

| Peptide sequence | chemical form | abbreviation |
|---|---|---|
| QRKIRVRLSA [SEQ ID NO: 13] | MAP | M28 |
| QKRIRVRLSA [SEQ ID NO: 14] | MAP | M29 |
| QRRIRVRLSA [SEQ ID NO: 15] | MAP | M30 |

For each peptides, MIC was calculated on three reference strains: *E. coli* ATCC 25922, *P. aeruginosa* ATCC 27853

(Gram negative) and *S. aureus* ATTC25923 (Gram positive). MIC values obtained from replacing M6 lysines with the arginines show that the replacement of lysine in position 2 with an arginine does not influence the antimicrobial activity of MAP (Table 8).

TABLE 8

MIC values of M6 modified peptides M28, M29 and M30

| Peptide | *E. coli* ATCC 25922 MIC (Molarity) | *P. aeruginosa* ATCC 27853 MIC (Molarity) | *S. aureus* ATCC 25923 MIC (Molarity) |
|---|---|---|---|
| M6 | $1.5 \times 10^{-6}$ | $7.6 \times 10^{-7}$ | $>4.9 \times 10^{-5}$ |
| M28 | $3.8 \times 10^{-7}$ | $7.6 \times 10^{-7}$ | $>1.2 \times 10^{-5}$ |
| M29 | $6.0 \times 10^{-6}$ | $6.0 \times 10^{-6}$ | $>1.2 \times 10^{-5}$ |
| M30 | $3.0 \times 10^{-6}$ | $1.2 \times 10^{-5}$ | $>1.2 \times 10^{-5}$ |

From this mini-library, the petide M28 was identified as particularly active against the Gram negative bacteria *E. coli* ATCC 25922 and *P. aeruginosa* ATCC 27853 with MIC values, expressed in molarity, respectively of $3.8 \times 10^{-7}$ and $7.6 \times 10^{-7}$ M.

From this mini-library, the peptide M28 was identified as particularly active against the Gram negative bacteria *E. coli* ATCC 25922 and *P. aeruginosa* ATCC 27853 with MIC values, expressed in molarity, respectively of $3.8 \times 10^{-7}$ and $7.6 \times 10^{-7}$ M.

EXAMPLES

Example 1

In one example, the tetrabranched MAP peptides with the amino acid sequence: QAKIRVRLSA [SEQ ID NO: 2], KIRVRLSA [SEQ ID NO: 3], QKKIRVRLSA [SEQ ID NO: 4] are used individually in a bacterial colony growth inhibition test. The test is conducted by incubating different concentrations of MAP peptides with *E. coli* (strain TG1) and plating bacterial cells on agar at a dilution such to allow for individual colonies counting. The following day, the number of colonies grown after treatment with the three MAP peptides is compared. The MAP peptides with sequence KIRVRLSA [SEQ ID NO: 3] and QKKIRVRLSA [SEQ ID NO: 4] exhibit a bactericidal activity on TG1 cells down to a concentration of 6.25 µg/ml.

Example 2

In an additional example, the minimum inhibitory concentration (MIC) of the tetrabranched MAP peptides having the sequence: QAKIRVRLSA [SEQ ID NO: 2], KIRVRLSA [SEQ ID NO: 3], QKKIRVRLSA [SEQ ID NO: 4] was calculated on different Gram negative bacterial strains. The MIC values of KIRVRLSA [SEQ ID NO: 3] and QKKIRVRLSA [SEQ ID NO: 4], expressed in molarity, are in the order of $10^{-6}$-$10^{-7}$ M for the Gram negative bacteria *E. coli* ATCC 25922 and *P. aeruginosa* ATCC 27853.

Example 3

In an additional example, the minimum inhibitory concentration (MIC) of the tetrabranched MAP peptides having the sequence: QAKIRVRLSA [SEQ ID NO: 2], KIRVRLSA [SEQ ID NO: 3], QKKIRVRLSA [SEQ ID NO: 4] was calculated on different Gram positive bacterial strains, such as *S. aureus* ATTC25923. The values of MIC computed for the three MAP peptides are in the order of $10^{-5}$ M.

Example 4

In another example, the minimal concentration able to kill 99.9% of the micro-organisms (MBC) of the tetrabranched MAP peptides having the sequence: QAKIRVRLSA [SEQ ID NO: 2], KIRVRLSA [SEQ ID NO: 3], QKKIRVRLSA [SEQ ID NO: 4], was evaluated. The MBCs were calculated on strains of *E. coli* ATCC 25922 and *P. aeruginosa* ATCC 27853 and were found to be equal to the corresponding MIC values for the same strains.

Example 5

In a further example, the haemolytic activity on human erythrocytes of the tetrabranched MAP having the sequence: KIRVRLSA [SEQ ID NO: 3], QKKIRVRLSA [SEQ ID NO: 4] was calculated. The percentage of haemolysis is calculated using the Parpart method by means of a calibration curve obtained incubating the erythrocytes with increasing concentrations of NaCl. At a concentration of 125 µg/ml QKKIRVRLSA [SEQ ID NO: 4] and KIRVRLSA [SEQ ID NO: 3] showed very poor haemolytic activity (less than 5%) after an incubation of 30 min. By contrast, after 19 hours of incubation, the haemolysis induced by QKKIRVRLSA [SEQ ID NO: 4] and KIRVRLSA [SEQ ID NO: 3] at 125 µg/ml is 7% and 19%, respectively.

Example 6

In another example, the tetrabranched MAP peptides having the sequence: QAKIRVRLSA [SEQ ID NO: 2], KIRVRLSA [SEQ ID NO: 3], QKKIRVRLSA [SEQ ID NO: 4] are tested in an in vitro assay, in which their cytotoxicity on murine macrophage J774 A.1 cells and on human HaCaT keratinocytes is determined by a colorimetric assay (MTT). As the concentration of MAP peptides increases, the vitality of J774 A.1 cells decreases, whilst human HaCaT keratinocytes are particularly resistant to the peptides even when administered at a concentration of 1 mg/ml.

Example 7

In a further example, the MAP peptide M6 (sequence QKKIRVRLSA [SEQ ID NO: 4]) demonstrated that it effectively binds the bacterial Lipopolysaccharide when it is passed on a sensorchip of a BIACORE instrument, previously sensitised with the same MAP peptide M6.

Example 8

In an additional example, the MAP peptides derived from "Alanine Scanning", conducted on the sequence of M6 peptide (Table 6) are each one used to calculate their minimum inhibitory concentration (MIC) on the bacterial strains *E. coli* ATCC 25922, *P. aeruginosa* ATCC 27853 and *S. aureus* ATTC25923. Alanine Scanning by replacing sequentially every amino acid of M6 with an alanine, allows to identify the critical residues responsible for bactericidal activity of the peptide. From this mini-library, a peptide was identified (M33) which proved to be particularly active against the Gram negative bacteria *E. coli* ATCC 25922 and *P. aeruginosa* ATCC 27853 with MIC values of $1.5 \times 10^{-6}$ M for both strains (Table 6).

Example 9

In an additional example, MAP peptides obtained by replacing the lysines (K) with arginines (R) of the MAP peptide M6 (Table 7) are each used to calculate their minimum inhibitory concentration (MIC) on the bacterial strains *E. coli* ATCC 25922, *P. aeruginosa* ATCC 27853 and *S.*

*aureus* ATTC25923. From this mini-library, a peptide was identified (M28) which proved to be particularly active against the Gram negative bacteria *E. coli* ATCC 25922 and *P. aeruginosa* ATCC 27853 with MIC values of $3.8 \times 10^{-7}$ and $7.6 \times 10^{-7}$ M, respectively (Table 8).

Materials and Methods

Selection of the Antibacterial Peptides from the Phage Library

The peptides able to have an antibacterial effect were selected using a phage library of random peptides of 10 mer, following standard protocols for the use of these libraries. The peptides were selected by means of three pannings. 1 ml of cells of *E. coli* strain TG1 at the $OD_{600}=0.1$ (about $0.8 \times 10^7$ cells) was centrifuged at 17000×g for 3 min. The pellet was re-suspended in 1 ml of PBS and incubated under slow agitation for about $10^{14}$ phages for 60 minutes at ambient temperature. Cells and phages were recovered after a centrifugation at 17000×g for 3 min. The supernatant was aspirated and the pellet washed 10 times with PBS-tween 0.1% to remove the phages not bound in the first selection round and washed with PBS-tween 0.5% in the subsequent rounds. The cells with the phages attached were centrifuged at 17000×g for 3 min and the pellet was re-suspended in 1 ml of elution buffer [0.2 M glycine-HCl (pH 2.2)] leaving under slow agitation for about 5 minutes at ambient temperature. The sample was centrifuged as done previously and the supernatant transferred into an Eppendorf tube and neutralised with 150 µL of 1M Tris-HCl (pH 9.1). 100 µL of eluted phage were used to infect 10 ml of *E. coli* TG1 in exponential growth phase for 30 min at 37° C. After the infection, the bacteria were centrifuged for 10 minutes at 3300×g, re-suspended in 1 ml of 2×TY (DESCRIVERE) and plated on agar containing ampicillin (100 µg/mL)-glucose (1%). After overnight incubation (o.n.) at 30° C., the colonies were recovered from the plate by adding 5-10 mL of 2×TY in such a way as to obtain an homogeneous suspension. 100 mL of 2×TY-ampicillin (100 µg/ml)-glucose (1%) were inoculated with 100 µl of a bacterial suspension until obtaining an $OD_{600}=0.4-0.5$, 10 ml of culture were drawn and infected with 100 µl of the phage helper VCS.M13 ($>10^{11}$ transforming unit (tu)/ml). The infected bacteria were centrifuged at 3300×g for 10 min, the recovered pellet was then re-suspended in 100 ml of 2×TY-ampicillin (100 µl/ml)-kanamycin (25 µg/ml) and agitated over night at 30° C. The phages were purified and concentrated for precipitation with PEG/NaCl (20% polyethylene glycol 6000-2.5 M NaCl) and re-suspended in 2 ml of PBS. The eluted phages were recovered, amplified and used for two more selection cycles. At the end of the process, the presence of specific phages for the bacterial surface was verified by ELISA assay.

Synthesis of the Peptides

The solid phase synthesis of the linear peptides was conducted by means of Syro MultiSynTech (WittenBochum, D) peptide synthesiser, using a resin of p-(2,4-dimethoxyphenyl-Fmoc-aminomethyl)-phenoxyacetamidonorleucyl-(4-methylbenzydryl-amine) (Rink-MBHA) and the chemistry of fluorenylmethoxycarbonyl (Fmoc). The de-protection reaction was obtained by adding 40% of piperidine in N-methylpyrrolidone and, for the attack reaction, N-hydroxybenzotriazole esters of F-moc-aminoacids prepared in situ were used for the conjugation reaction. The peptides were detached from the resin and simultaneously de-protected using a trifluoroacetic acid/thioanisole/ethaneditiol/water mixture (93/2/3/2) for 3 hours at ambient temperature. The peptides were purified by means of reverse phase HPLC on a Vydac C18 semi-preparative column using a 30 min gradient of buffer B from 0% to 100% (buffer A: 0.1% trifluoroacetic acid/water; buffer B: 0.1% trifluoroacetic acid/methanol).

The synthesis of the multiple tetraramified antigenic peptides (MAP) was achieved by a solid phase procedure on Wang $Fmoc_4$-$K_2$—K-A resin, using Fmoc chemistry. The MAP peptides were separated from the support using standard techniques and purified by means of reverse phase HPLC. The peptides were checked by mass spectrometry.

Test of Antibacterial Activity on *E. Coli* Strain Tg1.

Antimicrobic tests were conducted incubating for 75 min at 37° C., 25 µL of *E. coli* at the $OD_{600}$ of 0.2 with 25 µl of MAP peptide dissolved in PBS at the various concentrations. The different incubations were further diluted 1:1000 in 2×TY medium and 100 µl were plated on solid 2×TY medium. The plates were left overnight at 30° C. and the individual grown colonies were counted and compared with a control, not treated with MAP peptide.

Minimum Inhibitory Concentration (MIC) determination

Reference strains (*Escherichia coli* ATCC 25922, *Pseudomonas aeruginosa* ATCC 27853, *Staphylococus aureus* ATCC 25923 and *Chryseobacterium meningosepticum* CCUG 4310) and several recent clinical isolates (including multidrug-resistant ones) of various species (Table 2) were used for conventional susceptibility testing experiments. Minimum Inhibitory Concentration (MIC) was determined by a standard microdilution assay as recommended by the National Commitee for Clinical Laboratory Standards (NCCLS) using cation-supplemented Mueller-Hinton (MH) broth (Oxoid Ltd. Basingstoke, UK) and a bacterial inoculum of $5 \times 10^4$ CFU per well, in a final volume of 100 µl. Results were recorded by visual inspection after 24 h of incubation at 37° C. Minimum Bactericidal Concentration (MBC), defined as the concentration at which $\geq 99.9\%$ of the bacterial inoculum is killed, was determined as recommended by the NCCLS after MIC testing.

Calculation of the Minimal Bactericidal Concentration (MBC)

The MBC is defined as the minimal concentration of antibiotic able to kill 99.9% of the micro-organisms of the original inoculation of the species in question. The MBC was determined as recommended by the National Committee for Clinical Laboratory Standards (NCCLS) on strains of *E. coli* ATCC 25922 and *P. aeruginosa* ATCC 27853.

Time-Kill Kinetics

Assay of bactericidal activity in time-kill experiments was carried out as follows. The peptide was added, at the desired concentration, to exponentially growing cultures of the test strain in MH broth containing a total inoculum of $5 \times 10^7$ CFU ($1 \times 10^7$ CFU/ml) at 37° C. Samples were drawn at different times and suitable dilutions were plated on MH agar to score the residual number of CFU. A culture without peptide was always grown in parallel as control.

Cytotoxicity Test by MTT

For cytotoxicity tests, different cell lines were used: murine myeloma cells SPO, hamster ovary epithelium cells CHO K 1, murine macrophage cells J774 A.1 and human keratinocytes HaCaT. The cells were plated in medium in RPMI 1640 (SPO and CHO K 1) and DMEM (J774 A.1 and HaCaT) with antibiotics and bovine foetal serum at 10%, in 96-well plates at the concentration of $6 \times 10^4$ (SPO, CHO K1 and J774 A.1) and $3 \times 10^4$ (HaCaT). Peptides, previously filtered with a 0.2 µm filter disk (Whatman), were added at various concentrations to the different cell lines and left in incubation over night at 37° C. Cell viability was determined adding the MTT tetrazolium salt at the concentration of 0.5 mg/ml and incubating for 90 min. The cells were solubilised with a solution at pH 4.5 containing SDS 10% and dimethylformamide 45% and read at the dual wavelength of 595/650 nm with a plate reader.

Effect of QAKIRVRLSA (M4), KIRVRLSA (M5) and QKKIRVRLSA (M6) on the *Pichia Pastoris* Yeast Strain X33

To a volume of 50 µl of culture of *Pichia pastoris* grown 24 hour at 30° C. in YPD (Yeast Extract/Peptone/Dextrose) medium, 50 µl of MAP peptides (2 mg/ml) were added and left in incubation 150 min at 37° C. Subsequently, 50 µl of each incubation were plated on YPD solid medium and it was allowed to grow for 48 hours at 30° C. The number of colonies grown was compared with a control, where the yeast was not treated with the MAP.

Stability to Serum and Plasmatic Protease

The various peptides in MAP form and the linear peptide (L1) were dissolved in $H_2O$ at the concentration of 10 mM and incubated with 10 µl of plasma and human serum for 2 and 24 hours at 37° C. To each sample were added 150 µl of methanol to block the proteolytic reaction; each sample was then centrifuged at 13,000 rpm for 2 min and to the supernatant were added 0.75 ml of 0.1% trifluoroacetic acid. The samples were analysed in reverse phase HPLC on a Vydac C18 semi-preparative column using a 30 min gradient of buffer B from 20% to 95% (buffer A: 0.1% trifluoroacetic acid/water; buffer B: 0.1% trifluoroacetic acid/methanol), to evaluate the presence of linear and MAP peptide after the proteolytic treatment.

Haemolysis

The haemolytic activity of the KIRVRLSA [SEQ ID NO: 3] (M5) and QKKIRVRLSA [SEQ ID NO: 4] (M6) peptides was evaluated by the Parpart erythrocyte osmotic resistance assay in NaCl. The percentage of haemolysis was calculated by means of a calibration curve obtained incubating the erythrocytes with increasing concentrations of NaCl and measuring the absorbance increase, due to haemolysis, at 540 nm. 0.9% NaCl solutions containing the MAP peptides at different concentrations were then prepared, whereto was added human blood in the ratio of 1:100 (v/v). The samples were left at ambient temperature for 30 min and 19 hours; subsequently, a portion was drawn for each incubation, centrifuged at 1500 rpm for 5 min and the absorbance of the super was measured with the spectrophotometer at 540 nm.

Beta-Galactosidase Activity Assay

The ability of the QAKIRVRLSA [SEQ ID NO: 2] (M4), KIRVRLSA [SEQ ID NO: 3] (M5) and QKKIRVRLSA [SEQ ID NO: 4] (M6) MAP peptides to perforate the bacterial membrane was evaluated measuring the activity of cytoplasmatic beta-galactosidase using as a substrate p-nitrophenyl-β-D-galactopyranoside (pNPG), which, digested by the beta-galactosidase, frees the p-nitro-phenolate detectable by spectrophotometric reading at 420 nm. In order to do this, *E. coli* cells of the strain ML-35 were used: they constitutively produce beta-galactosidase and their lactose transporter is deactivated. The bacterial cells were drawn during the logarithmic growth phase ($OD_{600}$=0.4-0.5) and re-suspended in phosphate buffer 10 mM containing NaCl 100 mM (pH 7.4) and 1.5 mM pNPG. At time zero, the peptide in MAP form was added at the final concentration of 16, 32 and 64 µg/ml and the absorbance change was measured at 420 nm.

DNA Binding Assay

Gel-retardation experiments were performed by mixing 200 ng of the *E. coli* plasmid vector pCEP4 (Invitrogen) with increasing amounts of M6 peptide in 20 µl of binding buffer (5% glycerol, 10 mM Tris-HCl (pH 8.0), 1 mM EDTA, 1 mM DTT, 20 mM KCl and 50 µg/ml BSA). The reaction mixtures were incubated at room temperature for 1 h. Subsequently, 4 µl of native loading buffer was added (40% saccarose, 0.25% bromophenol blue) and an aliquot of 12 µl was applied to a 1% agarose gel electrophoresis in 1 mM Tris borate-EDTA buffer.

Confocal Laser-Scanning Microscopy

TG1 *E. coli* cells were grown overnight in 2×TY. After dilution 1:10 in cell medium, 5×1 ml aliquots were prepared, washed two times with 10 mM sodium phosphate buffer (PBS) pH 7.4 and incubated in 200 µl of a tetramethylrhodamine (TMR) labelled peptide solution (20 µg/ml in PBS) for 5 min at 37° C. After washing with PBS, each aliquot of the cells were resuspended in 200 µl of PBS and kept in the dark at 37° C. respectively for 2, 30, 60, 120, 240 min. The cells were then mounted in a glass slide and observed with a Bio-Rad MRC600 laser scanning confocal microscope (CLSM). Fluorescent images were obtained with a 568 nm bandpass filter for excitation of TMR. Software merging of images was carried out by using a COMOS software. A double-staining method was developed to visualize, with two marker at the same time, the membrane perturbating activity induced by M6 on bacteria. The following fluorochromes were used: (i) the propidium iodide (PI), a DNA-staining fluorescent; and (ii) the green fluorescent probe fluoresceine iso-thiocyanate (FITC), which is unable to traverse the cytoplasmic membrane of cells unless permeabilized by a peptide. *E. coli* cells were prepared as described above and treated with 5, 10, 20, 40 µg/mL of peptide for 30 min at 37° C. The cells were then washed with PBS, and a FITC solution (6 µg/ml in PBS) was added. After 30 min at 37° C., the FITC solution was removed and the cells were washed again with PBS. A DAPI solution (6 µg/ml in PBS) was then added to the cells. Fluorescent images were obtained with a 568 nm bandpass filter for excitation of TMR and with a 488 nm bandpass filter for FITC.

BIBLIOGRAPHY

1. Zasloff M. Antimicrobial peptides of multicellular organisms. *Nature.* 2002 Jan. 24; 415(6870):389-95.
2. Boman, H. G. Peptide antibiotics and their role in innate immunity. *Annu. Rev. Immunol.* 1995; 13, 61-92.
3. Steiner H, Hultmark D, Engstrom A, Bennich H, Boman H G. Sequence and specificity of two antibacterial proteins involved in insect immunity. *Nature.* 1981 Jul. 16; 292 (5820):246-8.
4. Selsted M E, Novotny M J, Morris W L, Tang Y Q, Smith W, Cullor J S. Indolicidin, a novel bactericidal tridecapeptide amide from neutrophils. *J Biol. Chem.* 1992 Mar. 5; 267(7):4292-5.
5. Agerberth B, Lee J Y, Bergman T, Carlquist M, Boman H G, Mutt V, Jornvall H. Amino acid sequence of PR-39. Isolation from pig intestine of a new member of the family of proline-arginine-rich antibacterial peptides. *Eur J Biochem.* 1991 Dec. 18; 202(3):849-54.
6. Romeo D, Skerlavaj B, Bolognesi M, Gennaro R. Structure and bactericidal activity of an antibiotic dodecapeptide purified from bovine neutrophils. *J Biol. Chem.* 1988 Jul. 15; 263(20):9573-5.
7. Lehrer R I, Ganz T. Defensins: endogenous antibiotic peptides from human leukocytes. Ciba Found Symp. 1992; 171:276-90; discussion 290-3. Review.
8. Agerberth B, Boman A, Andersson M, Jornvall H, Mutt V, Boman H G. Isolation of three antibacterial peptides from pig intestine: gastric inhibitory polypeptide (7-42), diazepam-binding inhibitor (32-86) and a novel factor, peptide 3910. *Eur J Biochem.* 1993 Sep. 1; 216(2):623-9.

9. Matsuzaki K. Why and how are peptide-lipid interactions utilized for self-defence?Magainins and tachyplesins as archetypes. *Biochim Biophys Acta*. 1999 Dec. 15; 1462(1-2):1-10.
10. Yang L, Weiss T M, Lehrer R I, Huang H W. Crystallization of antimicrobial pores in membranes: magainin and protegrin *Biophys J*. 2000 October; 79(4):2002-9.
11. Shai Y. Mechanism of the binding, insertion and destabilization of phospholipid bilayer membranes by alpha-helical antimicrobial and cell non-selective membrane-lytic peptides *Biochim Biophys Acta*. 1999 Dec. 15; 1462(1-2): 55-70.
12. Hanckok R E. Peptide antibiotics. *Lancet*. 1997 Feb. 8; 349(9049):418-22. Review.
13. Bessalle R, Kapitkovsky A, Gorea A, Shalit I, Fridkin M. All-D-magainin: chirality, antimicrobial activity and proteolytic resistance. *FEBS Lett*. 1990 Nov. 12; 274(1-2): 151-5.
14. Wade D, Boman A, Wahlin B, Drain C M, Andreu D, Boman H G, Merrifield R B. All-D amino acid-containing channel-forming antibiotic peptides. *Proc Natl Acad Sci U S A*. 1990 June; 87(12):4761-5.
15. Merrifield E L, Mitchell S A, Ubach J, Boman H G, Andreu D, Merrifield R B. D-enantiomers of 15-residue cecropin A-melittin hybrids. *Int J Pept Protein Res*. 1995 September-October; 46(3-4):214-20.
16. Brotz H, Josten M, Wiedemann I, Schneider U, Gotz F, Bierbaum G, Sahl H G. Role of lipid-bound peptidoglycan precursors in the formation of pores by nisin, epidermin and other lantibiotics. *Mol Microbiol*. 1998 October; 30(2): 317-27.
17. Lam K S, Salmon S E, Hersh E M, Hruby V J, Kazmierski W M, Knapp R J. A new type of synthetic peptide library for identifying ligand-binding activity. *Nature*. 1991 Nov. 7; 354(6348):82-4.
18. Houghten R A, Pinilla C, Blondelle S E, Appel J R, Dooley C T, Cuervo J H. Generation and use of synthetic peptide combinatorial libraries for basic research and drug discovery. *Nature*. 1991 Nov. 7; 354(6348):84-6.
19. Smith G P. Filamentous fusion phage: novel expression vectors that display cloned antigens on the virion surface. *Science*. 1985 Jun. 14; 228(4705):1315-7.
20. Tam J P. Synthetic peptide vaccine design: synthesis and properties of a high-density multiple antigenic peptide system. *Proc Natl Acad Sci USA*. 1988 August; 85(15):5409-13.
21. Tam J P, Lu Y A, Yang J L. Antimicrobial dendrimeric peptides. *Eur J. Biochem*. 2002 February; 269(3):923-32.
22. Bracci L, Falciani C, Lelli B, Lozzi L, Runci Y, Pini A, De Montis M G, Tagliamonte A, Neri P. Synthetic peptides in the form of dendrimers become resistant to protease activity. *J Biol. Chem*. 2003 Nov. 21; 278(47):46590-5.
23. Lozzi L, Lelli B, Runci Y, Scali S, Bernini A, Falciani C, Pini A, Niccolai N, Neri P, Bracci L. Rational design and molecular diversity for the construction of anti-alpha-bungarotoxin antidotes with high affinity and in vivo efficiency. *Chem Biol*. 2003 May; 10(5):411-7.
24. Lehrer R I, Barton A, Daher K A, Harwig S S, Ganz T, Selsted M E. Interaction of human defensins with *Escherichia Coli*. Mechanism of bactericidal activity. *J Clin Invest*. 1989 August; 84(2):553-61.
25. Hancock R E, Lehrer R. Cationic peptides: a new source of antibiotics. *Trends Biotechnol*. 1998 February; 16(2): 82-8. Review.
26. Demitri M T, Velucchi M, Bracci L, Rustici A, Porro M, Villa P, Ghezzi P. *Journal of Endotoxin Research. Vol*. 3(6), 1996, pp. 445-454.
27. Yang S T, Shin S Y, Lee C W, Kim Y C, Hahm K S, Kim J I. Selective cytotoxicity following Arg-to-Lys substitution in tritrpticin adopting a unique amphipathic turn structure. *FEBS Lett*. 2003 Apr. 10; 540(1-3):229-33.

The invention claimed is:

1. An antibacterial peptide consisting of one of the following amino acid sequences from the amino to the carboxylic terminal QAKIRVRLSA [SEQ ID NO: 2], QKKIRVRLSA [SEQ ID NO: 4] or KIRVRLSA [SEQ ID NO: 3].

2. The peptide of claim 1 being of linear form.

3. An antibacterial peptide consisting of one of the following amino acid sequences from the amino to the carboxylic terminal QAKIRVRLSA [SEQ ID NO: 2], QKKIRVRLSA [SEQ ID NO: 4] or KIRVRLSA [SEQ ID NO: 3], wherein said peptide is in linear form multimerised on a skeleton of polyacrylamide, on a skeleton of dextrane units or on a skeleton of ethylene glycol units.

4. The peptide of claim 1, being in the form of Multiple Antigenic Peptide (MAP), having the following formula:

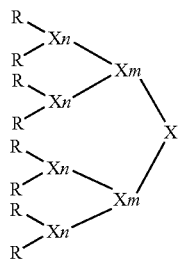

in which R is the peptide as claimed in claim 1, X is a trifunctional molecule; m=0 or 1; n=0, if m=0; n=0 or 1 if m=1.

5. The MAP peptide according to claim 4, wherein X is an amino acid having at least two functional aminic group.

6. The MAP peptide according to claim 5, wherein X is lysine, ornithine, nor-lysine or amino alanine.

7. The MAP peptide according to claim 4, wherein X is aspartic acid or glutamic acid.

8. The MAP peptide according to claim 4, wherein X is propylene glycol, succinic acid, diisocyanates or diamines.

9. A pharmaceutical composition comprising a pharmaceutically acceptable and effective quantity of the peptide according to claim 1.

10. The pharmaceutical composition according to claim 9, in the form of eyewash, mouth wash, ointment, or solution for topical use.

11. A disinfectant and/or detergent preparation with antibacterial activity comprising the peptide according to claim 1.

12. Food products and/or cosmetic products and/or homeopathic products comprising the peptide according to claim 1.

* * * * *

```
                        SEQUENCE LISTING

<160> NUMBER OF SEQ ID NOS: 15

<210> SEQ ID NO 1
<211> LENGTH: 10
<212> TYPE: PRT
<213> ORGANISM: Artificial
<220> FEATURE:
<223> OTHER INFORMATION: synthetic

<400> SEQUENCE: 1

Gln Glu Lys Ile Arg Val Arg Leu Ser Ala
1               5                   10

<210> SEQ ID NO 2
<211> LENGTH: 10
<212> TYPE: PRT
<213> ORGANISM: Artificial
<220> FEATURE:
<223> OTHER INFORMATION: synthetic

<400> SEQUENCE: 2

Gln Ala Lys Ile Arg Val Arg Leu Ser Ala
1               5                   10

<210> SEQ ID NO 3
<211> LENGTH: 8
<212> TYPE: PRT
<213> ORGANISM: Artificial
```

```
<220> FEATURE:
<223> OTHER INFORMATION: synthetic

<400> SEQUENCE: 3

Lys Ile Arg Val Arg Leu Ser Ala
1               5

<210> SEQ ID NO 4
<211> LENGTH: 10
<212> TYPE: PRT
<213> ORGANISM: Artificial
<220> FEATURE:
<223> OTHER INFORMATION: synthetic

<400> SEQUENCE: 4

Gln Lys Lys Ile Arg Val Arg Leu Ser Ala
1               5                   10

<210> SEQ ID NO 5
<211> LENGTH: 10
<212> TYPE: PRT
<213> ORGANISM: Artificial
<220> FEATURE:
<223> OTHER INFORMATION: synthetic

<400> SEQUENCE: 5

Ala Lys Lys Ile Arg Val Arg Leu Ser Ala
1               5                   10

<210> SEQ ID NO 6
<211> LENGTH: 10
<212> TYPE: PRT
<213> ORGANISM: Artificial
<220> FEATURE:
<223> OTHER INFORMATION: synthetic

<400> SEQUENCE: 6

Gln Lys Ala Ile Arg Val Arg Leu Ser Ala
1               5                   10

<210> SEQ ID NO 7
<211> LENGTH: 10
<212> TYPE: PRT
<213> ORGANISM: Artificial
<220> FEATURE:
<223> OTHER INFORMATION: synthetic

<400> SEQUENCE: 7

Gln Lys Lys Ala Arg Val Arg Leu Ser Ala
1               5                   10

<210> SEQ ID NO 8
<211> LENGTH: 10
<212> TYPE: PRT
<213> ORGANISM: Artificial
<220> FEATURE:
<223> OTHER INFORMATION: synthetic

<400> SEQUENCE: 8

Gln Lys Lys Ile Ala Val Arg Leu Ser Ala
1               5                   10

<210> SEQ ID NO 9
<211> LENGTH: 10
<212> TYPE: PRT
<213> ORGANISM: Artificial
<220> FEATURE:
<223> OTHER INFORMATION: synthetic
```

```
<400> SEQUENCE: 9

Gln Lys Lys Ile Arg Ala Arg Leu Ser Ala
1               5                   10

<210> SEQ ID NO 10
<211> LENGTH: 10
<212> TYPE: PRT
<213> ORGANISM: Artificial
<220> FEATURE:
<223> OTHER INFORMATION: synthetic

<400> SEQUENCE: 10

Gln Lys Lys Ile Arg Val Ala Leu Ser Ala
1               5                   10

<210> SEQ ID NO 11
<211> LENGTH: 10
<212> TYPE: PRT
<213> ORGANISM: Artificial
<220> FEATURE:
<223> OTHER INFORMATION: synthetic

<400> SEQUENCE: 11

Gln Lys Lys Ile Arg Val Arg Ala Ser Ala
1               5                   10

<210> SEQ ID NO 12
<211> LENGTH: 10
<212> TYPE: PRT
<213> ORGANISM: Artificial
<220> FEATURE:
<223> OTHER INFORMATION: synthetic

<400> SEQUENCE: 12

Gln Lys Lys Ile Arg Val Arg Leu Ala Ala
1               5                   10

<210> SEQ ID NO 13
<211> LENGTH: 10
<212> TYPE: PRT
<213> ORGANISM: Artificial
<220> FEATURE:
<223> OTHER INFORMATION: synthetic

<400> SEQUENCE: 13

Gln Arg Lys Ile Arg Val Arg Leu Ser Ala
1               5                   10

<210> SEQ ID NO 14
<211> LENGTH: 10
<212> TYPE: PRT
<213> ORGANISM: Artificial
<220> FEATURE:
<223> OTHER INFORMATION: synthetic

<400> SEQUENCE: 14

Gln Lys Arg Ile Arg Val Arg Leu Ser Ala
1               5                   10

<210> SEQ ID NO 15
<211> LENGTH: 10
<212> TYPE: PRT
<213> ORGANISM: Artificial
<220> FEATURE:
<223> OTHER INFORMATION: synthetic

<400> SEQUENCE: 15
```

```
Gln Arg Arg Ile Arg Val Arg Leu Ser Ala
1               5                   10
```